(12) United States Patent
Hasenberg et al.

(10) Patent No.: US 7,326,820 B2
(45) Date of Patent: Feb. 5, 2008

(54) SYSTEM AND METHOD FOR PURIFYING HEPTANE

(75) Inventors: Daniel M. Hasenberg, Kingwood, TX (US); Mitchell D. Refvik, Bartlesville, OK (US); Christopher Raymond Tully, Borger, TX (US); Michael S. Hankinson, Bartlesville, OK (US); Clyde Stewart Denton, Borger, TX (US); Dale Solaas, Fritch, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 481 days.

(21) Appl. No.: 10/927,908

(22) Filed: Aug. 27, 2004

(65) Prior Publication Data

US 2005/0080311 A1    Apr. 14, 2005

Related U.S. Application Data

(60) Provisional application No. 60/498,773, filed on Aug. 29, 2003.

(51) Int. Cl.
 C07C 7/12    (2006.01)
 C07C 7/13    (2006.01)
 C07C 7/00    (2006.01)
 C07C 7/148   (2006.01)
 C07C 7/17    (2006.01)

(52) U.S. Cl. .............. 585/820; 585/800; 585/809; 585/811

(58) Field of Classification Search ............ 585/809, 585/811, 800, 820
See application file for complete search history.

(56) References Cited

U.S. PATENT DOCUMENTS

| | | | | |
|---|---|---|---|---|
| 2,494,335 A | * | 1/1950 | Dutson | 585/314 |
| 2,554,251 A | * | 5/1951 | Hudson | 585/667 |
| 2,594,557 A | | 4/1952 | Hirschler | |
| 2,813,851 A | | 11/1957 | McKay | |
| 3,351,547 A | * | 11/1967 | Drehman | 585/741 |
| 4,880,604 A | * | 11/1989 | Koves | 422/220 |
| 5,171,923 A | | 12/1992 | Dickson et al. | |
| 5,443,697 A | | 8/1995 | Berg | |
| 6,005,157 A | | 12/1999 | Lee et al. | |
| 6,156,950 A | | 12/2000 | Ragil et al. | |

OTHER PUBLICATIONS

Harmer et al., Towards the Sulfuric Acid of Solids, 10 Adv. Mater. 15, 1255-1257 (1998).*
T. Otsu et al., Monomer-Isomerization Polymerizations of Heptene-2, Heptene-3, and Octene-2 with Ziegler-Natta Catalyst, 10 Polymer Letters 601-604 (1972).*
Technical Data Sheet for LZY-84 1/16" Extrudate, Customtec, 1 pg.
International Search Report, PCT/US2004/028015, Feb. 21, 2005, 4 pgs.
Written Opinion of the International Searching Authority, PCT/US2004/028015, 6 pgs.
Funke, Hans H., et al., "Separations of Cyclic, Branched, and Linear Hydrocarbon Mixtures through Silicalite Membranes," Ind. Eng. Chem. Res., 1997, vol. 36, pp. 137-143, XP 002316753.
Plettenberg, Horst., et al., "Oxidative Removal of Isoalkanes from N-Alkanes by Iodine Tris (trifluoroacetate)," XP002316754, 1 pg.—1982.
Database WPI, Section Ch, Week 198719, Derwent Publications Ltd., London, GB., Class E17, AN 1987-134001, XP002316755, 1 pg.
Database WPI, Section Ch, Week 199844, Derwent Publications Ltd., London, GB., Class E19, AN 1998-509522, XP002316756, 2 pgs.

* cited by examiner

*Primary Examiner*—Jill Warden
*Assistant Examiner*—Randy Boyer
(74) *Attorney, Agent, or Firm*—Conley Rose, P.C.; Rodney B. Carroll

(57) ABSTRACT

Removing impurities from a heptane stream by contacting the heptane stream with an acidic catalyst, wherein the contacting reduces a concentration of one or more close boiling impurities, one or more olefins, or both. The impurities are isomerized via contact with the acidic catalyst into species that possess lower octane levels or that do not possess boiling points as near to the boiling point of n-heptane, which promotes separation of the impurities via distillation. Close boiling impurities may include such compounds as cis-1,2-dimethylcyclopentane and methylcyclohexane or may be compounds having boiling points at a standard pressure of 760 Torr in the range of about 96.5 to about 100.5 degrees Celsius including such compounds as cis-1,2-dimethylcyclopentane and methylcyclohexane. The concentration of cis-1,2-dimethylcyclopentane and methylcyclohexane may be reduced by at least about 25 and 10 percent by weight, respectively. The concentration of olefins, as measured by the Bromine Index, may be reduced by at least about 25 percent by weight.

39 Claims, 4 Drawing Sheets

US 7,326,820 B2

SYSTEM AND METHOD FOR PURIFYING HEPTANE

CROSS-REFERENCE TO RELATED APPLICATIONS

This application claims the benefit of U.S. provisional application No. 60/498,773 entitled "System and Method for Purifying Heptane" and filed on Aug. 29, 2003, which is hereby incorporated by reference herein in its entirety.

FIELD OF THE INVENTION

This invention relates generally to a system for purifying heptane via a catalytic reaction, and, more particularly, to contacting a heptane stream with an acidic catalyst in order to reduce the concentration of close boiling impurities and produce primary reference fuel grade heptane.

BACKGROUND OF THE INVENTION

Primary reference fuel (PRF) grade heptane contains a minimum of 99.75 weight percent normal heptane (or "n-heptane") and is generally produced by purifying a heptane stream that contains less than 99.75 weight percent n-heptane. Among the heptane streams available as a feed for production of PRF heptane may be a pure grade heptane, which contains a minimum of 99.0 weight percent n-heptane. Impurities common to heptane streams include the close boiling $C_7$ isomers methylcyclohexane and cis-1,2 dimethylcyclopentane among other $C_7$ olefin, $C_7$ paraffin, and cyclic impurities. Heptane streams, including pure grade heptane and PRF heptane, are valuable commercially as fuels. Additionally, PRF heptane may be valuable as a high purity solvent, such as in pharmaceutical applications. In order to obtain the purity levels associated with PRF heptane, fractionation has been used to separate the normal heptane (n-heptane) from impurities such as other $C_7$ isomers.

Typically, one or more fractionations of a heptane feedstock stream are employed to produce PRF heptane. The high purity of PRF heptane may cause it to require more than one fractionating step. In addition, super-atmospheric fractionation may improve the ability to separate impurities. As a result, the rate of production of PRF heptane may only be a portion of the production rate of heptane grades containing higher levels of contaminants, such as, for example, pure grade heptane. Thus, fractionation of a heptane stream in order to obtain PRF heptane may be both capital intensive and expensive to operate.

The octane number of a fuel is an expression of antiknock properties commonly measured according to ASTM D 2699, ASTM D 2700, or an average of the two. The octane of pure n-heptane is zero, but olefinic and cyclic impurities in a heptane product have significantly higher octane numbers, which raise the octane number of the heptane product such as PRF heptane. Thus, the higher the percentage of impurities removed from a heptane stream, even after attaining the 99.75 weight percent specification for PRF heptane, the closer the octane number is to zero, and the more competitive the product. Thus, a need exists for improved methods of purifying heptane.

SUMMARY OF THE INVENTION

In an embodiment, a method is provided for removing impurities from a heptane stream comprising contacting the heptane stream with an acidic catalyst, wherein said contacting reduces a concentration of one or more close boiling impurities, one or more olefins, or both in the heptane stream. The impurities are isomerized via contact with the acidic catalyst into species that possess lower octane levels or that do not possess boiling points as near to the boiling point of n-heptane, which promotes separation of the impurities via distillation. In an embodiment, impurities are isomerized and removed via distillation to produce a heptane stream comprising at least about 99.75 weight percent heptane (e.g., PRF heptane). In an embodiment, close boiling impurities may include such compounds as cis-1,2-dimethylcyclopentane and methylcyclohexane. In an embodiment, close boiling impurities may be those having boiling points at a standard pressure of 760 Torr in the range of about 96.5 to about 100.5 degrees Celsius. In an embodiment, the concentration of cis-1,2-dimethylcyclopentane may be reduced by at least about 25 percent by weight. In another embodiment, the concentration of methylcyclohexane may be reduced by at least about 10 percent by weight. In another embodiment, the concentration of olefins, as measured by the Bromine Index, may be reduced by at least about 25 percent by weight.

In an embodiment, a system for producing a primary reference fuel (PRF) grade heptane is provided. In an embodiment, the system includes a heptane feed, a reactor for contacting the heptane feed with an acidic catalyst, and a fractionation for further separating impurities from said heptane feed after contacting to produce said PRF heptane (minimum 99.75 weight percent purity). In an embodiment, the system includes a dryer for controlling the level of moisture in the heptane feed.

DETAILED DESCRIPTION OF EMBODIMENTS

Figure 1:
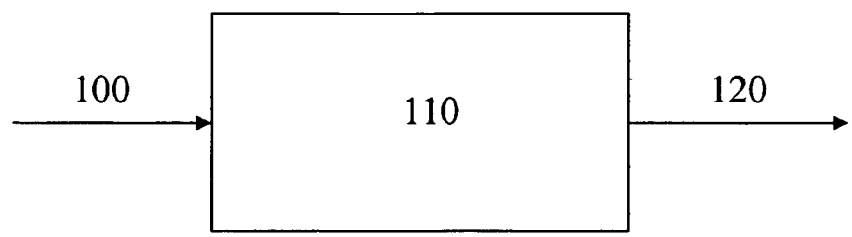
FIG. 1 is a block diagram illustrating an embodiment of a feed, reactor, and product stream in accordance with the present invention.

FIG. 1 represents an embodiment of the present invention that reduces the concentration of certain impurities in a heptane stream. In the embodiment illustrated by FIG. 1, a heptane feed stream 100 enters a contacting vessel 110 (e.g., reactor) containing an acidic catalyst. A catalytic isomeric reaction occurs when the heptane stream 100 enters the contacting vessel 110 and is contacted with the acidic catalyst. The reaction between impurities in the heptane stream and the acidic catalyst causes an isomeric conversion of impurities. Thus, the vessel output 120 contains lower concentrations of certain impurities that have undergone isomerization.

The heptane stream provided may be any heptane source or stream containing n-heptane. In an embodiment, the heptane stream contains at least about 90 weight percent n-heptane. In another embodiment, the heptane stream contains at least about 94 weight percent n-heptane. In another embodiment, the heptane stream is a pure grade heptane, which contains a minimum 99.0 weight percent n-heptane. In an embodiment, the heptane stream provided is obtained by fractionation of a $C_7$ fraction of a refinery stream or unit such as a fractionation unit. In addition to n-heptane, such a heptane stream typically contains impurities, including other $C_7$ isomers. In an embodiment, the heptane feed stream typically includes n-heptane and one or more of the additional components listed below in Table I, along with boiling point data:

TABLE I

Example Components of a Heptane Stream

| Compound | Boiling Point @ 760 Torr (° C.) |
|---|---|
| 1,1-dimethylcyclopentane | 87.83 |
| 2,3-dimethylpentane | 89.78 |
| 2-methylhexane | 90.06 |
| cis-1,3-dimethylcyclopentane | 90.78 |
| 3-methylhexane | 91.83 |
| trans-1,3-dimethylcyclopentane | 91.72 |
| 3-ethylpentane | 93.50 |
| n-heptane | 98.44 |
| isooctane | 99.06 |
| cis-1,2-dimethylcyclopentane | 99.56 |
| methylcyclohexane | 100.94 |

In an embodiment, the heptane stream includes at least about 94 weight percent n-heptane. In another embodiment, the heptane stream is a pure grade heptane that typically includes n-heptane and at least one or more of the additional components listed below in Table II, along with boiling point and physical property data:

TABLE II

Components of a Pure Grade Heptane

| Compound | Chemical Formula | Boiling point @760 Torr ° C. | ° F. | Standard Heat of Formation (BTU/lb mole) |
|---|---|---|---|---|
| cis-1,3-dimethylcyclopentane | $C_7H_{14}$ | 90.77 | 195.386 | $-7.14 \times 10^4$ |
| trans-1,3-dimethylcyclopentane | $C_7H_{14}$ | 91.73 | 197.114 | $-7.23 \times 10^4$ |
| trans-1,2-dimethylcyclopentane | $C_7H_{14}$ | 91.87 | 197.366 | $-7.37 \times 10^4$ |
| 2-ethyl-1-pentene | $C_7H_{14}$ | 94.0 | 210.20 | $-4.72 \times 10^4$ |
| trans-3-heptene | $C_7H_{14}$ | 95.67 | 204.206 | $-4.70 \times 10^4$ |
| cis-3-heptene | $C_7H_{14}$ | 95.75 | 204.35 | $-4.49 \times 10^4$ |
| trans-2-heptene | $C_7H_{14}$ | 97.95 | 208.31 | $-4.71 \times 10^4$ |
| cis-2-heptene | $C_7H_{14}$ | 98.41 | 209.138 | $-4.52 \times 10^4$ |
| n-heptane | $C_7H_{16}$ | 98.43 | 209.174 | $-9.64 \times 10^4$ |
| 2,2,4-trimethyl pentane (isooctane) | $C_7H_{16}$ | 99.238 | 210.628 | $-1.11 \times 10^5$ |
| cis-1,2-dimethylcyclopentane | $C_7H_{14}$ | 99.53 | 211.154 | $-7.11 \times 10^4$ |
| methylcyclohexane | $C_7H_{14}$ | 100.934 | 213.631 | $-8.18 \times 10^4$ |
| 2,4,4-trimethyl-1-pentene | $C_7H_{14}$ | 101.44 | 214.592 | $-6.29 \times 10^4$ |

In an embodiment, pure grade heptane includes from about 99.0 to about 99.75 weight percent heptane. In another embodiment, pure grade heptane includes from about 99.3 to about 99.45 weight percent heptane; from about 0.030 to about 0.040 weight percent trans-1,2-dimethylcyclopentane (trans-1,2-DMCP); from about 0.25 to about 0.50 weight percent cis-1,2 dimethylcyclopentane (cis-1,2-DMCP); from about 0.050 to about 0.07 weight percent methylcyclohexane; and from about 0.015 to about 0.10 miscellaneous components.

In an embodiment, the isomeric conversion described herein should reduce the concentration of one or more close boiling impurities in the output 120, as compared to the concentration of close boiling impurities in the feed 100. For purposes of this application, close boiling impurities are impurities that possess boiling points close to that of n-heptane. In another embodiment, close boiling impurities are those that possess boiling points in the range from about 96.5 to about 100.5 degrees Celsius at a pressure of about 760 Torr, where n-heptane possesses a boiling point under similar conditions of about 98.4 degrees Celsius. In another embodiment, close boiling impurities are those that possess boiling points in the range from about 97.0 to about 100.3 degrees Celsius at a pressure of about 760 Torr. In another embodiment, close boiling impurities are those that possess boiling points in the range from about 97.5 to about 100.0 degrees Celsius at a pressure of about 760 Torr. In particular, cis-1,2-dimethylcyclopentane (cis-1,2-DMCP) may be one close boiling impurity found in a heptane stream. The concentration of cis-1,2-DMCP in the heptane stream provided is typically less than one weight percent. In an embodiment, the heptane stream contains at least 90 weight percent heptane and less than 1 weight percent cis-1,2-dimethylcyclopentane. In another embodiment, the heptane stream contains at least 90 weight percent heptane, less than 1 weight percent cis-1,2-dimethylcyclopentane, and less than 1 weight percent methylcyclohexane. A portion of the close boiling impurities are isomerized in the contacting vessel into compounds that, for purposes of this application, are considered impurities other than close boiling impurities (or "non-close boiling impurities"). As a result, impurities in the output 120 may be more readily separable, as compared to impurities in the feed 100, from n-heptane via fractionation.

In an embodiment, the isomerization reaction described herein reduces the concentration of the close boiling impurity cis-1,2-DMCP by at least about 25 weight percent. In another embodiment, the isomerization reaction described herein reduces the concentration of the close boiling impurity cis-1,2-DMCP by at least about 50 weight percent. In another embodiment, the isomerization reaction described herein reduces the concentration of the close boiling impurity cis-1,2-DMCP by at least about 70 weight percent. In another embodiment, the isomerization reaction described herein reduces the concentration of the close boiling impurity cis-1,2-DMCP by at least about 85 weight percent. The cis-1,2-DMCP is converted to trans-1,2-dimethylcyclohexane or methylcyclohexane (MCH), or to other species. The most thermodynamically favored isomerization of cis-1,2-DMCP is to MCH. In addition, any $C_7$ olefins in the reactor feed 100 (e.g., see Tables I and II) are thermodynamically favored to isomerize to MCH. Conversion of any $C_7$ olefins to MCH is desirable since reduction of $C_7$ olefins reduces the octane number of the mixture. Conversion to MCH is also significant because the boiling point of MCH (100.934 degrees Celsius at 760 Torr) is about 3 degrees Celsius higher than the boiling point of n-heptane. In contrast, cis-1,2-DMCP possesses a boiling point only about 1 degree Celsius higher than n-heptane. Thus, removing MCH is typically less costly than removing cis-1,2-DMCP in any fractionation step(s) subsequent to the isomerization. Alternatively, the cis-1,2-DMCP not converted to MCH may be converted to other isomeric species, such as those having boiling points more than about 10 degrees Celsius different from n-heptane.

In an embodiment, methylcyclohexane may be a close boiling impurity found in a heptane stream. In an embodiment, the isomerization reaction described herein reduces the concentration of the close boiling impurity methylcyclohexane by at least about 10 weight percent. In another embodiment, the isomerization reaction described herein reduces the concentration of the close boiling impurity methylcyclohexane by at least about 25 weight percent. In another embodiment, the isomerization reaction described herein reduces the concentration of the close boiling impurity methylcyclohexane by at least about 50 weight percent.

The isomerization described herein may also reduce the concentration of olefins as measured by the Bromine Index. The Bromine Index is defined as milligrams of bromine necessary to titrate 100 grams of sample. In an embodiment, the isomerization herein reduces the concentration of olefins according to the Bromine Index by at least about 25 percent by weight. In another embodiment, the isomerization herein reduces the concentration of olefins according to the Bromine Index by at least about 40 percent by weight. In another embodiment, the isomerization herein reduces the concentration of olefins according to the Bromine Index by at least about 50 percent by weight.

The reactor or contacting vessel 110 may be any reactor suitable for contacting n-heptane with an isomerization catalyst in order to execute the catalytic reaction described herein, such as, for example, a continuous flow or batch reactor, whether used in a laboratory or commercial production scale environment. In an embodiment, the vessel 110 is a continuous fixed bed reactor. In another embodiment, the vessel 110 is a continuous upflow packed bed catalytic reactor where both the feed 100 and output products 120 are liquids. In another embodiment, the vessel 110 is a recirculation isomerization reactor where all or part of the reactor effluent is recycled to the feed until a set conversion of impurities is achieved. In another embodiment, the vessel 110 is a batch isomerization reactor. In another embodiment, the vessel 110 is a single pass fixed bed reactor. The vessel 110 contains an acidic catalyst and the heptane feed 100 is contacted with the acidic catalyst within the vessel. The contacting of a heptane stream with an acidic catalyst reduces the concentration of, among other things, cis-1,2-DMCP. In the output 120, the concentration of certain impurities, particularly $C_7$ cyclics and olefins, and/or more particularly close boiling impurities, is reduced, as discussed above, compared to the concentration of such impurities in the heptane feed 100. The output 120 transfers the contacted heptane from the vessel 110, and typically to a further separation step or steps.

Any catalyst, such as an acid catalyst, suitable for converting one or more of the close boiling impurities to non-close boiling impurities may be used. The acidic catalyst may be in aqueous, liquid, or solid form. Examples of such acidic catalysts commonly known in the art and available commercially include chlorosulfonic acid, sulfuric acid, aluminum chloride, Amberlyst®-15, Filtrol®-24 clay, Nafion®, generally any "X" or "Y" zeolite catalyst with substantial acidity, and in particular LZY-84 solid acidic zeolite catalyst. Amberlyst®-15 is a styrene-divinylbenzene copolymer having pendant sulfonic acid groups, and is produced by Rohm and Haas®. Filtrol®-24 clay is a sulfuric acid washed clay catalyst supplied by the Engelhard Corporation. Nafion® is a copolymer of perfluoroethylene (also known as tetrafluoroethylene) and a perfluorovinyl ether containing attached sulfonyl acid groups, and is produced by E. I. DuPont De Nemours and Company of Wilmington, Del. LZY-84 is a solid acidic zeolite catalyst, such as is available from Customtec of Des Plaines, Ill.

In a desirable embodiment of the system and method described herein, the catalyst is an LZY-84 solid acidic zeolite catalyst. Such an LZY-84 solid acidic zeolite catalyst is a "Y" zeolite, and may be an extrudate produced from an LZY-84 synthetic hydrogen form faujasite molecular sieve and an inorganic alumina binder. In an embodiment, each extruded piece is comprised of from about 45 to about 95 weight percent zeolite and from about 5 to about 55 weight percent inorganic alumina binder. In another embodiment, each extruded piece is comprised of from about 65 to about 90 weight percent zeolite and from about 10 to about 35 weight percent inorganic alumina binder. In another embodiment, each extruded piece is comprised of from about 75 to about 85 weight percent zeolite and from about 15 to about 25 weight percent inorganic alumina binder. In an embodiment, the extrudate has a unit cell size of about 20 to about 30 angstroms, a surface area of about 600 to about 700 square meters per gram, and bulk density of about 35 to about 40 pounds per cubit foot. Typical physical properties of these extrudates include a unit cell size of about 24.50 angstroms, surface area of about 650 square meters per gram, and bulk density of about 39 pounds per cubic foot.

Figure 2:
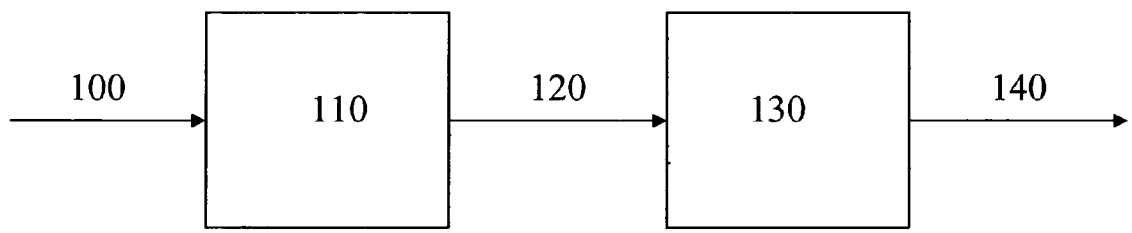
FIG. 2 is a block diagram illustrating an embodiment of a feed, reactor, reactor product, fractionator, and product stream in accordance with the present invention.

In an embodiment, the isomerization reaction described herein may take place among any number of fractionation steps, as long as at least one fractionation step follows the isomerization reactor. FIG. 2 illustrates an embodiment of the present invention in which one or more fractionators 130 are added to the embodiment illustrated by FIG. 1. In the embodiment illustrated by FIG. 2, the reactor product 120 is fed to the one or more fractionators 130, which is designed to further purify the heptane. In an embodiment, the fractionation provided includes one fractionator. In another embodiment, the fractionation provided includes two fractionators. The presence of even small amounts of close boiling impurities, such as cis-1,2-DMCP, in a heptane stream interferes with the ability to produce further purified products, such as PRF heptane. In the reactor 110, a fraction of the close boiling impurities present in the original feed 100 is isomerized into non-close boiling impurities, such as described previously. Thus, the conversion in the contacting vessel 110 of impurities possessing boiling points within 1 degree Celsius of n-heptane to species, such as MCH, which possess boiling points at least 3 degrees Celsius different from n-heptane, may make it possible to employ a less costly fractionation in order to separate a higher percentage of the impurities. In an embodiment, the fractionation provided separates impurities having boiling points at a standard pressure of 760 Torr that are outside the range of about 98.0 degrees to about 99.5 degrees Celsius.

Figure 5:
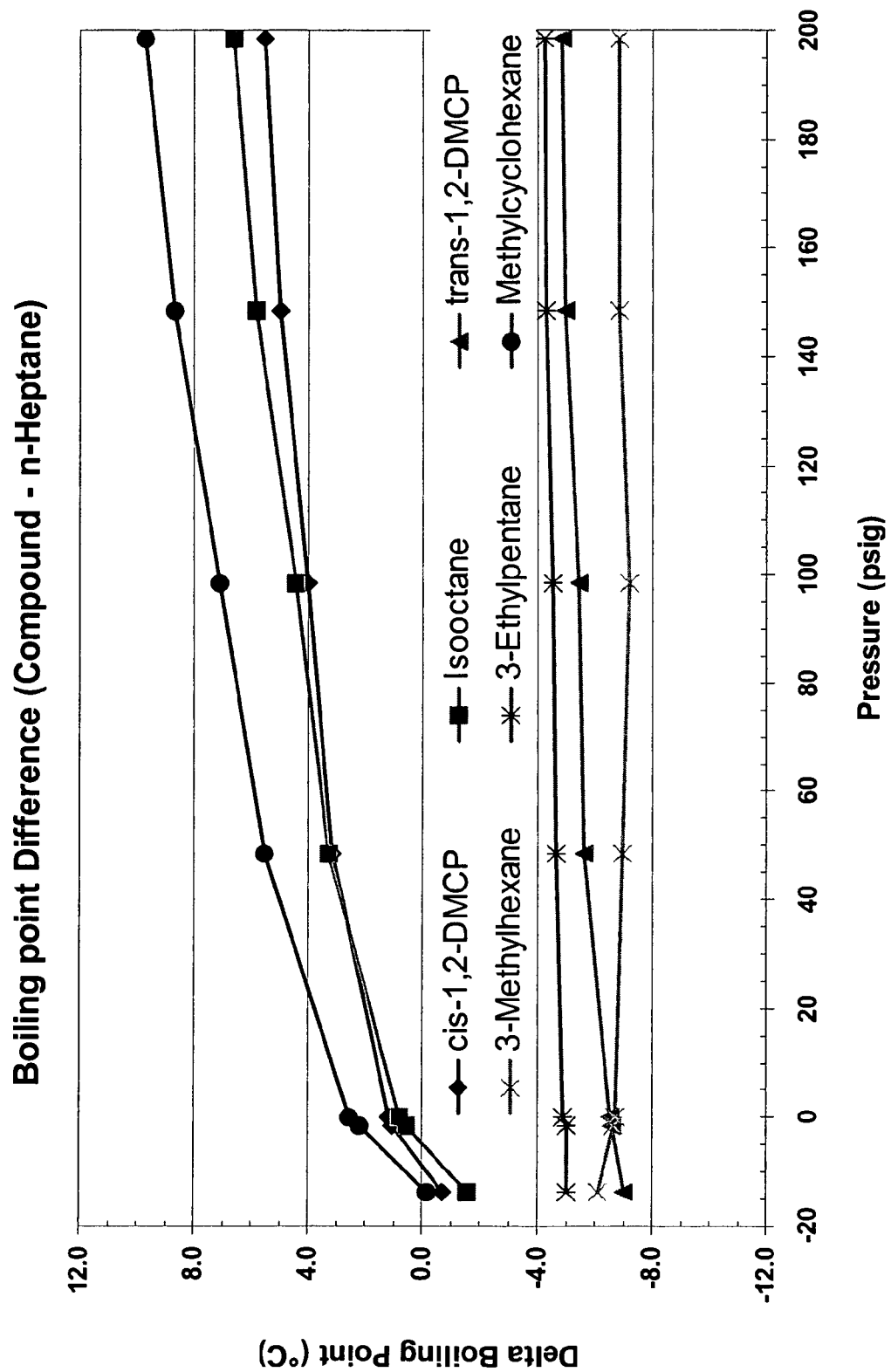
FIG. 5 is a chart illustrating the change in the difference between the boiling point of n-heptane and the boiling points of various impurities as pressure varies.

The fractionation may be operated at non-standard pressures in order to manipulate the boiling points of stream constituents. In an embodiment, the fractionation provided occurs at sub-atmospheric pressures. In another embodiment, the fractionation provided occurs at super-atmospheric pressures such that the boiling points of stream components are separated by more degrees than at sub-atmospheric and atmospheric pressures. FIG. 5 charts data illustrating the affect of varying pressure on the difference between the boiling point of n-heptane and the boiling points of several close boiling impurities. A chart value of zero indicates no difference between the boiling point of n-heptane and the boiling point of the impurity. Impurities represented in the chart include cis-1,2-dimethylcyclopentane (cis-1,2-DMCP), 2,2,4-trimethylpentane (isooctane), trans-1,2-dimethylcyclopentane (trans-1,2-DMCP), 3-methylhexane, 3-ethylpentane, and methylcyclohexane (MCH). The data indicate that boiling point differences between some impurities and n-heptane increase as pressure increases. In an embodiment, the fractionation occurs at from about −20 to about 500 psig. In another embodiment, the fractionation occurs at from about 0 to about 250 psig. In another embodiment, the fractionation occurs at from about 5 to about 100 psig. Example boiling point data in Table III illustrates the effect of a super-atmospheric pressure of 80 psig on boiling point:

TABLE III

Boiling Point Data at 80 psig

| Compound | Normal Boiling Point | 80 psig boiling Point |
|---|---|---|
| n-heptane | 98.43° C. | 177° C. |
| cis-1,2-DMCP | 99.53° C. | 181° C. |
| methylcyclohexane | 100.93° C. | 184° C. |

The further purified heptane products from such a fractionation may include at least one primary reference fuel (PRF) grade heptane product stream 140. In an embodiment, the PRF heptane stream 140 contains at least about 99.75 weight percent n-heptane. In another embodiment, the PRF heptane stream 140 contains at least about 99.80 weight percent n-heptane. In another embodiment, the PRF heptane stream 140 contains at least about 99.85 weight percent n-heptane. In another embodiment, the PRF heptane stream 140 contains at least about 99.9 weight percent n-heptane. In another embodiment, the PRF heptane stream contains no more than about 0.1 weight percent cis-1,2-DMCP. In another embodiment, the PRF heptane stream contains no more than about 0.05 weight percent cis-1,2-DMCP. In another embodiment, the PRF heptane stream contains no more than about 0.01 weight percent cis-1,2-DMCP. In another embodiment, the PRF heptane stream contains no more than about 0.005 weight percent cis-1,2-DMCP. In another embodiment, the PRF heptane stream contains no more than about 0.001 weight percent cis-1,2-DMCP. The purity of the PRF heptane stream may also be expressed in terms of Bromine Index. In an embodiment, the PRF heptane stream has a Bromine Index of no more than about 3. In an embodiment, the PRF heptane stream has a Bromine Index of no more than about 2. In an embodiment, the PRF heptane stream has a Bromine Index of no more than about 1. In an embodiment, the PRF heptane stream has a Bromine Index of no more than about 0.5.

Figure 4:
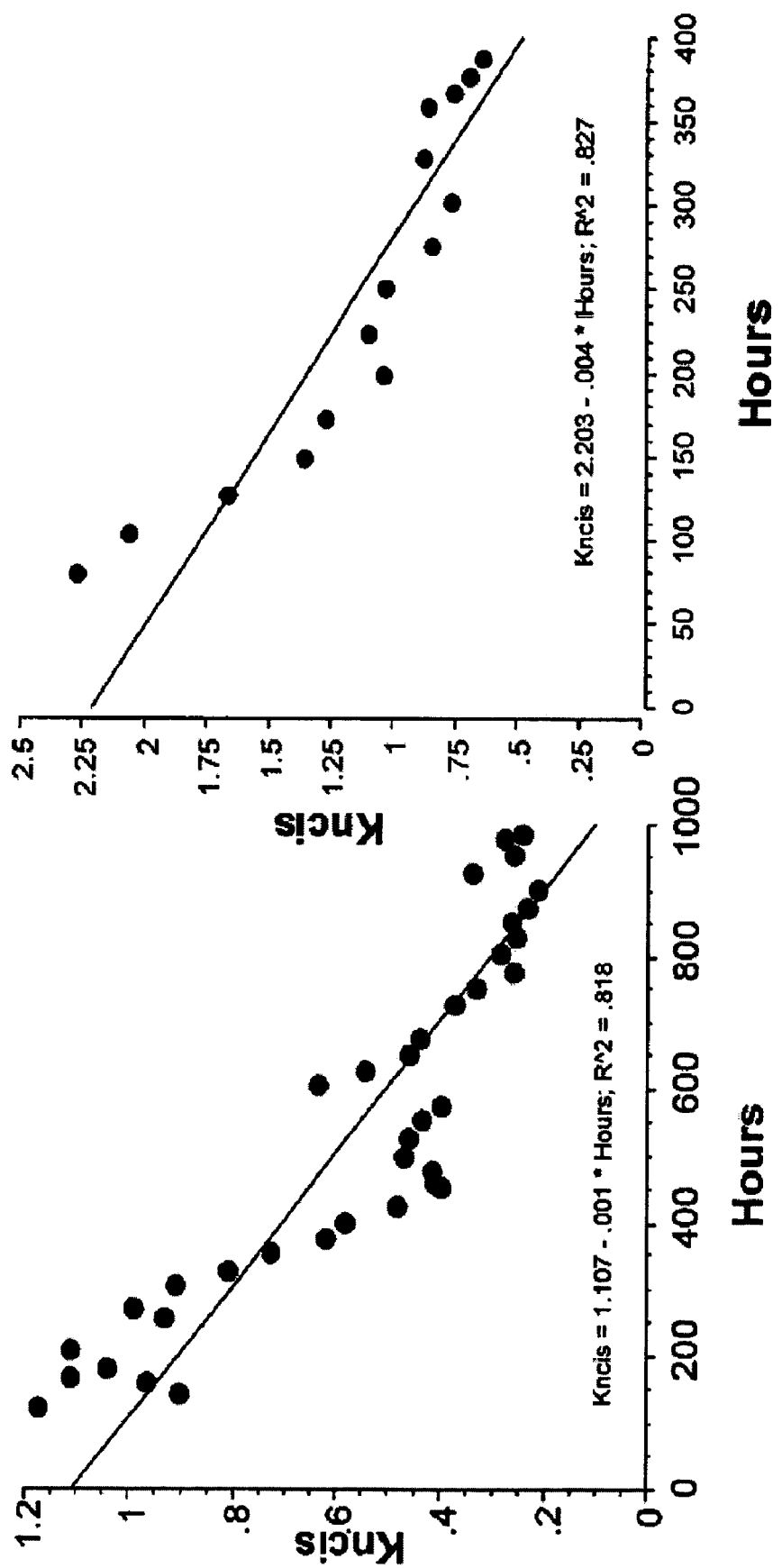
FIG. 4 is a pair of plots showing the normalized rate constant for removal of cis-1,2 dimethylcyclopentane over time for an embodiment of the present invention.

FIG. 4 is a pair of plots of normalized rate constant K for cis-1,2-DMCP removal versus time. The rate constant is normalized to 212 degrees Fahrenheit (100 degrees Celsius), and is defined by the following equation (using an activation energy of 20,000 BTU/lbmole): $K_{ncis\text{-}1,2\text{-}DMCP}=WHSV*\ln(cis\text{-}1,2_{feed}/cis\text{-}1,2_{product})\exp(-20,000/(1.987*(WAT°F+459.6)-14.992))$; where $cis\text{-}1,2_{feed}$ and $cis\text{-}1,2_{product}$ are the concentrations of cis-1,2-DMP in the feed and product, respectively, in weight percent, WAT is the weight average temperature expressed in degree Fahrenheit, and WHSV is the weight hourly space velocity defined as the weight of the feed (e.g., heptane) processed per hour, divided by the weight of the catalyst employed. As the plots indicate, the rate of the isomeric conversion reaction in the contacting vessel 110 may fall over time, in other words catalyst activity decreases with time. Without intending to be limited by theory, it is believed that this decrease in rate constant over time may be caused at least in part by catalyst coking, by moisture present in the heptane feed 100, by moisture in the catalyst in the reactor 110, or by combinations thereof. Thus, controlling of the moisture content in the reaction and/or controlling catalyst coking may help reduce catalyst deactivation and increase catalyst run life.

Figure 3:
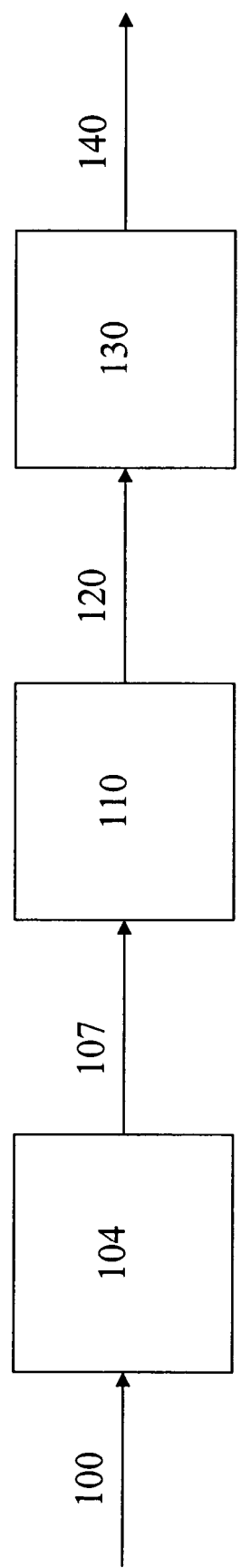
FIG. 3 is a block diagram illustrating an embodiment of the primary reference fuel grade heptane production system of the present invention.

In an embodiment further illustrated by FIG. 3, the heptane feed 100 is dried by addition of a dryer 104 to the embodiment illustrated by FIG. 2. The heptane feed 100 first passes through the dryer 104, then the dried feed 107 enters a contacting vessel 110, and the output 120 may transfer the product to one or more fractionators 130 for further separation of impurities. The dryer 104 controls the moisture (or water) content in the feed 107 to the contacting vessel 110. The drying material and/or process may be any drying material and/or process known to those skilled in the art. Examples of drying materials that may be appropriate include type 4A, type 5A, and 13X molecular sieves, alumina, and silica gel. In an embodiment, three angstrom molecular sieves, Type 3A, are used in the dryer 104 to remove moisture from the feed 100. The moisture level, or dew point, of the dried feed 107 may impact the rate of the reaction that reduces the concentration of close boiling impurities in the contacting vessel. Thus, employing a dryer may help maintain a desirable level of isomerization of close boiling impurities in the contacting vessel 110. In an embodiment, passing the feed 100 through the dryer 104 results in a moisture (water) content of no more than about 10 parts per million by weight in the dried feed 107. In another embodiment, passing the feed 100 through the dryer 104 results in a moisture (water) content of no more than about 3 parts per million by weight in the dried feed 107. In another embodiment, passing the feed 100 through the dryer 104 results in a moisture (water) content of no more than about 1 part per million by weight in the dried feed 107. Moisture content may be measured by various methods including via Karl-Fischer titration, use of an on-line dew-point analyzer, or by gas chromatographic techniques.

In addition to controlling the level of moisture in the feed 100, moisture (water) on the catalyst in the reactor 110 may be controlled, as it may affect catalyst activity. Drying of the catalyst may be achieved prior to contacting with the heptane stream in the reactor 110. In addition, the catalyst may be dried at any time during the course of production in order to boost activity. In an embodiment, the catalyst is dried by heating the catalyst for several hours in flowing nitrogen. In another embodiment, the catalyst should be dried at about 200 degrees Celsius in flowing nitrogen, then cooled to ambient temperature. In another embodiment, once the catalyst has been dried, exposure to air, or any source of oxygen, is avoided.

In addition to or in lieu of controlling the moisture in the reactor (either in the heptane feed 100, in the catalyst in the reactor 110, or both), other process variables may be adjusted such as WAT, WHSV, or both to address a drop in rate constant such as that shown in FIG. 4.

The catalyst deactivates slowly with time, so the weight average temperature (WAT) in the reactor may be raised steadily to maintain a desirable conversion rate. WAT is commonly defined as the sum of n internal thermocouple temperatures in the reactor 110 divided by n ($(t_1+t_2+ \ldots t_n)/n$). In an embodiment, both inlet and outlet temperatures are controlled, rather than only outlet temperature. In an embodiment where LZY-84 zeolite catalyst is employed, the start of run WAT is about 85 degrees Celsius and the end of run WAT is from about 165 to about 175 degrees Celsius, where the rate of daily increase of the WAT controls the amount of cis-1,2-DMCP in the reactor 110 effluent. In another embodiment, the WAT range is from about 60 degree Celsius to about 300 degrees Celsius. In another embodiment, the WAT range is from about 75 degree Celsius to about 220 degrees Celsius. In another embodiment, the WAT range is from about 85 degree Celsius to about 180 degrees Celsius. Another consideration is that at high enough temperatures, heptane cracking begins to occur. Thus, reactor temperatures are limited at all times by the rate of heptane cracking. In an embodiment, the heptane cracking reaction sets an upper limit on reactor WAT of about 300 degrees Celsius.

Increasing WAT of reactor 110 may be one way of compensating for deactivation of catalyst caused by moisture. However, raising reactor 110 temperature may increase coking on the catalyst, which accumulates to also decrease catalyst activity, and may not be removed by drying in flowing nitrogen. Thus, the moisture level in the dried heptane feed 107 may be conducive to an extended catalyst life by allowing temperatures to be kept lower, thereby minimizing coking. In an embodiment, the catalyst in the reactor reflects a change in WAT of from about 1 degree Celsius to about 10 degrees Celsius for about 1 weight percent of coke deposition. In another embodiment, the catalyst in the reactor reflects a change in WAT of from about 1 degree Celsius to about 5 degrees Celsius for about 1 weight percent of coke deposition. In another embodiment, the catalyst in the reactor reflects a change in WAT of from about 1 degree Celsius to about 2.5 degrees Celsius for about 1 weight percent of coke deposition.

In an embodiment of the purification method provided herein, the WHSV is from about 0.1 to about 10. In another embodiment, the WHSV is from about 0.1 to about 6. In another embodiment, the WHSV is from about 0.5 to about 5. In another embodiment, the WHSV is from about 1 to about 4. In another embodiment, the WHSV is from about 1.5 to about 3. In another embodiment, the WHSV is from about 1.5 to about 2.5.

In general, there is a trade-off between reactor 110 throughput as measured by WHSV and catalyst deactivation as measured by conversion of cis-1,2-DMCP. If constant conversion is desired and WHSV is increased, then WAT will have to be raised in order to maintain constant conversion. With increasing WAT, however, the catalyst will deactivate due to coking, so run lengths will decrease. Thus, maximizing run length means adjusting the WAT to meet the maximum allowable cis-1,2-DMCP concentration in the product 120. In an embodiment, the WAT corresponds to a WHSV of the dried heptane stream 107 through the reactor 110 of between about 1.5 and about 2.5. In an embodiment, the rate of LZY-84 zeolite catalyst deactivation at a WHSV between about 1.5 and about 2.5 comprises a change in WAT of about 2 degrees Celsius per day at about 85 wt % cis-1,2-DMCP conversion.

Other reactor parameters to be controlled include pressure and the length-to-diameter ratio (L/D), or reactor size. In an embodiment, the pressure is sufficient to keep heptane in the liquid phase. In another embodiment, the pressure is at least about equal to the vapor pressure of the heptane at the temperature employed. In another embodiment, the pressure is at least about 10 psig. In an embodiment, the L/D should be in the range from about 3 to about 35. In another embodiment, the L/D should be in the range from about 5 to about 30. In another embodiment, the L/D should be in the range from about 6 to about 25.

In an embodiment, catalyst activity is regenerated by burning coke off catalyst from the isomerization. In some embodiments, conditions effective for regenerating the catalyst may include temperatures from about 350 to about 600 degrees Celsius. In other embodiments, the catalyst is regenerated at a temperature in the range of 350 to 550 degrees Celsius. The regeneration if performed by burning coke off the catalyst in the presence of an oxygen containing gas. In some embodiments, coke is burned off the catalyst (the catalyst is regenerated) using air. In other embodiments, air is diluted with an inert gas. In some embodiment the inert gas may be argon, nitrogen or mixtures thereof. In some embodiments, the oxygen containing gas contains 0.1 to 21 percent, by volume, oxygen. In other embodiments, the oxygen containing gas contains is 0.2 to 15 percent by volume oxygen; alternatively 0.25 to 10 percent by volume oxygen; alternatively 0.5 to 6 percent, by volume oxygen. The time can be any time needed by the temperature and oxygen concentration conditions use to effectively bun the coke off the catalyst. In some embodiments, the regeneration time is 30 minutes to 24 hours. In other embodiment the regeneration time is between 2 and 12 hours. In yet another embodiment, the regeneration time is from 4 to 10 hours. As an example, a reactor prepared for catalyst regeneration may be purged with ambient nitrogen for 30 minutes to remove flammable material. After purging the reactor bed may be heated with hot nitrogen to a temperature in the range of 350 to 550 degrees Celsius, followed by bleeding air into the nitrogen steam such that the gas comprises from 0.25 to 0.5 percent, by volume, oxygen. Maximum bed temperature may be controlled by adjusting air flow. After oxygen breakthrough, the air bleed into the nitrogen stream may be increased to obtain a gas comprising 1.2 percent, by volume, oxygen, or as high a concentration of oxygen as is allowed, until the inlet and exit oxygen content are equal. Subsequently, the reactor may be purged of oxygen and moisture with hot nitrogen, at least about 550 degrees Celsius, and then purged and cooled with ambient nitrogen prior to re-introducing feed stocks to the reactor.

EXAMPLES

The following examples, 1 through 10, are merely representative of aspects of the present invention and, as one skilled in the art would recognize, the present invention may be practiced without many of the aspects illustrated by the examples.

Example 1

One drop of chlorosulfonic acid was added to about 1 ml of a heptane sample in a glass vessel and stirred for four hours. The sample was then washed three times with deionized water. The results from the analysis of the starting and ending hydrocarbon phase are shown in Table IV.

TABLE IV

|  | n-heptane (wt %) | Combined cis-1,2-DMCP and MCH (wt %) |
|---|---|---|
| starting material | 99.441 | 0.476 |
| after acid treatment | 99.876 | 0.004 |

The results in Table IV show that treatment with acids may selectively remove the unwanted close boiling impurities cis-1,2-DMCP and MCH from n-heptane while not reacting with n-heptane.

The data in Examples 2 through 5 were obtained using a 1-inch inner diameter flow reactor. The reactor was 316 stainless steel construction, and it was 30 inches long. The catalyst was packed in the center of the reactor, and glass beads were used to fill the remaining volume above and below the active catalyst inside the reactor. Temperatures were controlled using an external electric furnace with three independent heating zones. The product analyses were determined using a Hewlett-Packard 5890 gas chromatograph equipped with a 50 meter boiling point column. Data entries for Examples 2 through 6 were recorded over time with a maximum time interval between first and last entries of about two days.

Example 2

In this example executed in downflow, acidized clay (Filtrol®-24) was used as the isomerization catalyst. The data in Table V show that the concentration of cis-1,2-DMCP could be reduced from 0.441 to as low as 0.282 weight percent in the temperature range of about 100° to 325° C. while the n-heptane concentration was reduced by less than 2 weight percent. This example shows that solid acids are an effective selective isomerization catalyst for removal of cis-1,2-DMCP. Also, this example shows that solid acidized clays are an effective selective isomerization catalyst for removal of cis-1,2-DMCP.

TABLE V

| Entry No. | Top Temp. (° C.) | Mid Temp. (° C.) | Bottom Temp. (° C.) | Lights (wt %) | n-heptane (wt %) | cis-1,2-DMCP (wt %) | MCH (wt %) | Catalyst | Catalyst (grams) | Flow Rate (cc/min) | Pressure (psig) | WHSV |
|---|---|---|---|---|---|---|---|---|---|---|---|---|
| 1 (feed) | 25 | 25 | 25 | 0.121 | 99.361 | 0.441 | 0.059 | Filtrol-24 | 75.0 | 3.4 | 50 | 2.72 |
| 2 | 74 | 95 | 100 | 0.122 | 99.369 | 0.435 | 0.059 | Filtrol-24 | 75.0 | 3.4 | 50 | 2.72 |
| 3 | 144 | 167 | 219 | 0.162 | 99.379 | 0.375 | 0.085 | Filtrol-24 | 75.0 | 3.4 | 50 | 2.72 |
| 4 | 165 | 193 | 225 | 0.170 | 99.374 | 0.358 | 0.098 | Filtrol-24 | 75.0 | 3.4 | 50 | 2.72 |
| 5 | 166 | 301 | 308 | 0.299 | 99.286 | 0.307 | 0.108 | Filtrol-24 | 75.0 | 4.5 | 50 | 3.56 |
| 6 | 256 | 351 | 317 | 1.817 | 97.864 | 0.233 | 0.086 | Filtrol-24 | 75.0 | 4.5 | 50 | 3.56 |
| 7 | 179 | 319 | 295 | 1.603 | 98.038 | 0.282 | 0.077 | Filtrol-24 | 75.0 | 4.5 | 50 | 3.56 |

Example 3

LZY-84 was used as the catalyst in a downflow experiment. Comparison of the results in Table VI to Example 2 show that this "Y" zeolite, LZY-84, as compared to the acidized clay catalyst employed in Example 2, achieves desirable removal of cis-1,2-DMCP at temperatures about 100 to 150 degrees Celsius lower.

TABLE VI

| Entry No. | Top Temp (° C.) | Mid Temp (° C.) | Bottom Temp (° C.) | Lights (wt %) | n-heptane (wt %) | cis-1,2-DMCP (wt %) | MCH (wt %) | Catalyst | Catalyst (grams) | Catalyst (mls) | Flow Rate (cc/min) | Pressure (psig) | WHSV |
|---|---|---|---|---|---|---|---|---|---|---|---|---|---|
| 1 (feed) | 20 | 20 | 20 | 0.125 | 99.355 | 0.442 | 0.060 | LZY-84 | 60.0 | 100.0 | 2.17 | 50 | |
| 2 | 175 | 202 | 199 | 14.503 | 85.075 | 0.124 | <0.010 | LZY-84 | 60.0 | 100.0 | 2.17 | 50 | 2.17 |
| 3 | 166 | 189 | 190 | 9.287 | 90.477 | 0.158 | <0.010 | LZY-84 | 60.0 | 100.0 | 2.17 | 50 | 2.17 |

Example 4

LZY-84 was again used as the isomerization catalyst, but this time in an upflow experiment. Results are shown in Table VII. The concentration of cis-1,2-DMCP was reduced below detection limits at temperatures in excess of about 170° C. In addition, the n-heptane concentration was maintained at greater than 99.0 weight percent for temperatures up to about 170° C. In comparison to Example 3, the results in Example 4 show that a greater percentage of cis-1,2-DMCP was removed at the same temperatures while reducing the amount of n-heptane loss.

TABLE VII

| Entry No. | Top Temp (° C.) | Mid Temp (° C.) | Bottom Temp (° C.) | Lights (wt %) | n-heptane (wt %) | Cis-1,2-DMCP (wt %) | MCH (wt %) | Catalyst | Catalyst (grams) | Catalyst (mls) | Flow Rate (cc/min) | Pressure (psig) | WHSV |
|---|---|---|---|---|---|---|---|---|---|---|---|---|---|
| 1 (feed) | 25 | 25 | 25 | 0.122 | 99.360 | 0.440 | 0.060 | LZY-84 | 50.0 | 104 | 1.0 | 300 | |
| 2 | 165 | 170 | 155 | 0.468 | 99.197 | 0.018 | 0.316 | LZY-84 | 50.0 | 104 | 1.0 | 300 | 1.20 |

TABLE VII-continued

| Entry No. | Top Temp (°C.) | Mid Temp (°C.) | Bottom Temp (°C.) | Lights (wt %) | n-heptane (wt %) | Cis-1,2-DMCP (wt %) | MCH (wt %) | Catalyst | Catalyst (grams) | Catalyst (mls) | Flow Rate (cc/min) | Pressure (psig) | WHSV |
|---|---|---|---|---|---|---|---|---|---|---|---|---|---|
| 3 | 172 | 175 | 163 | 0.814 | 98.812 | <0.001 | 0.374 | LZY-84 | 50.0 | 104 | 1.0 | 300 | 1.20 |
| 4 | 185 | 188 | 177 | 2.185 | 94.486 | <0.001 | 0.330 | LZY-84 | 50.0 | 104 | 1.0 | 300 | 1.20 |

Example 5

Data for Example 5, shown in Table VIII, shows that by using higher temperatures (i.e., greater than 180° C.), the concentration of MCH can be reduced as well as the concentration of cis-1,2-DMCP. The feed for this experiment was 5.7 weight percent MCH in pure grade n-heptane, and the experiment was done in upflow.

TABLE VIII

| Entry No. | Top Temp (°C.) | Mid Temp (°C.) | Bottom Temp (°C.) | Lights (wt %) | n-heptane (wt %) | Cis-1,2-DMCP (wt %) | MCH (wt %) | Catalyst | Catalyst (grams) | Catalyst (mls) | Flow Rate (cc/min) | Pressure (psig) | WHSV |
|---|---|---|---|---|---|---|---|---|---|---|---|---|---|
| 1 (feed) | 25 | 25 | 25 (feed) | 0.114 | 93.791 | 0.376 | 5.702 | LZY-84 | 60.0 | 100.0 | 0.76 | 300 | |
| 2 | 186 | 184 | 172 | 6.671 | 88.805 | 0.00 | 4.382 | LZY-84 | 60.0 | 100.0 | 0.60 | 300 | 0.76 |
| 3 | 188 | 188 | 178 | 15.99 | 80.32 | 0.080 | 3.274 | LZY-84 | 60.0 | 100.0 | 0.60 | 300 | 0.76 |

Example 6

Data for Example 6, shown in Table IX, shows the isomerization rate of cis-1,2-DMCP as a function of temperature using fresh "Y" zeolite, LZY-84 catalyst. The concentration of n-heptane can be maintained above 99.0% while removing virtually all of the cis-1,2-DMCP. This example was in upflow.

TABLE IX

| Entry No. | Top Temp (°C.) | Mid Temp (°C.) | Bottom Temp (°C.) | Lights (wt %) | n-heptane (wt %) | Cis-1,2-DMCP (wt %) | MCH (wt %) | Catalyst | Catalyst (grams) | Catalyst (mls) | Flow Rate (cc/min) | Pressure (psig) | WHSV |
|---|---|---|---|---|---|---|---|---|---|---|---|---|---|
| 1 (feed) | 20 | 20 | 20 | 1.210 | 99.360 | 0.441 | 0.059 | LZY-84 | 47.9 | 104 | 1.0 | 300 | |
| 2 | 24 | 24 | 21 | 0.132 | 99.363 | 0.400 | 0.089 | LZY-84 | 47.9 | 104 | 1.0 | 300 | 1.25 |
| 3 | 60 | 60 | 55 | 0.130 | 99.379 | 0.404 | 0.071 | LZY-84 | 47.9 | 104 | 1.0 | 300 | 1.25 |
| 4 | 53 | 52 | 44 | 0.130 | 99.427 | 0.376 | 0.066 | LZY-84 | 47.9 | 104 | 1.0 | 300 | 1.25 |
| 5 | 78 | 77 | 64 | 0.133 | 99.441 | 0.359 | 0.067 | LZY-84 | 47.9 | 104 | 1.0 | 300 | 1.25 |
| 6 | 93 | 92 | 81 | 0.130 | 99.420 | 0.275 | 0.062 | LZY-84 | 47.9 | 104 | 1.0 | 300 | 1.25 |
| 7 | 100 | 100 | 85 | 0.133 | 99.445 | 0.355 | 0.066 | LZY-84 | 47.9 | 104 | 1.0 | 300 | 1.25 |
| 8 | 127 | 125 | 101 | 0.171 | 99.532 | 0.210 | 0.086 | LZY-84 | 47.9 | 104 | 1.0 | 300 | 1.25 |
| 9 | 121 | 149 | 124 | 0.632 | 93.442 | <0.001 | 0.238 | LZY-84 | 47.9 | 104 | 1.2 | 300 | 1.50 |
| 10 | 159 | 156 | 130 | 1.363 | 98.268 | <0.001 | 0.369 | LZY-84 | 47.9 | 104 | 1.2 | 300 | 1.50 |
| 11 | 167 | 164 | 136 | 1.291 | 98.330 | <0.001 | 0.379 | LZY-84 | 47.9 | 104 | 1.2 | 300 | 1.50 |
| 12 | 142 | 142 | 124 | 0.587 | 99.035 | <0.001 | 0.377 | LZY-84 | 47.9 | 104 | 1.2 | 300 | 1.50 |

The data in Examples 7 and 8 were obtained using a 2-inch inner diameter flow reactor. The reactor was 316 stainless steel construction, and it was 48 inches long. The catalyst was packed in the reactor, and inert α-alumina (Alundum) was used to dilute the active catalyst inside the reactor. Temperatures were controlled using an external electric furnace with three independent heating zones. The isomerization reaction was operated in this continuous upflow reactor for 12 weeks. Initial process conditions were chosen from Example 6. An initial space velocity of 1.0 WHSV and WAT of 100° C. were chosen. The reactor was run continuously, 24 hours/day. The product analyses were determined using a Hewlett-Packard 5890 gas chromatograph equipped with a 50 meter boiling point column.

Also in Examples 7 and 8, an LZY-84 solid acidic zeolite catalyst was employed in the reactor. The LZY-84 catalyst was dried by heating to 225 degrees Celsius for four hours in flowing nitrogen. The heptane feed to the reactor was dried over Type 3A molecular sieve beads, such as are commercially available from Aldrich. The Type 3A molecular sieves have a pore size that limits adsorption to only water (and ammonia), and heptane is excluded from adsorbing on Type 3 sieves. Initially, the mole sieve drier was changed out every 60 hours. That period was subsequently shortened to 24-36 hours beginning with about the 700 hour point in Example 7, and for the entire duration of Example 8. Samples of the reactor product were taken about every four hours and analyzed by GC to determine component concentrations. WAT for Examples 7 and 8 was defined as the weighted (by weight of catalyst) average of internal thermocouple temperatures divided by the number (4) of internal thermocouples.

Example 7

This experiment had a duration of about 1,000 hours on-stream. Data from analyses of the reactor feed are shown in Table X, and data from the reactor effluent are shown in Table XI. Temperature (WAT) was raised in response to catalyst deactivation in order to keep the cis-1,2-DMCP concentration in the effluent at 0.085 weight percent. No attempts were made to regenerate the catalyst by burning off the coke at the end of the run. Predictions for catalyst run length may be made using the correlation of $k_{ncis\text{-}1,2\text{-}DMCP}=1.107-0.0010*\text{Hours(onstream)}$, $R^2=0.82$.

TABLE X

Reactor Feed Analyses

| On-line Time (hours) | t-1,2-DMCP (wt %) | n-heptane (wt %) | Misc. (wt %) | c-1,2-DMCP (wt %) | MCH (wt %) | Br Index (mgBr/100 gms) |
|---|---|---|---|---|---|---|
| 0 | 0.034 | 99.388 | 0.019 | 0.472 | 0.062 | |
| 100 | 0.034 | 99.392 | 0.019 | 0.465 | 0.068 | |
| 201.5 | 0.035 | 99.393 | 0.019 | 0.468 | 0.062 | |
| 303 | 0.036 | 99.366 | 0.052 | 0.46 | 0.062 | |
| 415 | 0.034 | 99.391 | 0.019 | 0.471 | 0.061 | 40.8 |
| 504 | 0.035 | 99.39 | 0.02 | 0.47 | 0.064 | |
| 617 | 0.034 | 99.368 | 0.039 | 0.475 | 0.061 | |
| 703 | 0.035 | 99.390 | 0.02 | 0.465 | 0.069 | |
| 805 | 0.035 | 99.374 | 0.037 | 0.47 | 0.063 | |
| 909 | 0.032 | 99.363 | 0.049 | 0.476 | 0.058 | |
| 979 | 0.035 | 99.393 | 0.020 | 0.467 | 0.062 | |

TABLE XI

Reactor Effluent Analyses

| Hours On-line | Top Temp (° C.) | Mid Temp (° C.) | Mid Temp (° C.) | Bot Temp (° C.) | WAT (° C.) | Pressure (psig) | Feed rate (lb/hr) | WHSV (hr-1) | Lights (wt %) |
|---|---|---|---|---|---|---|---|---|---|
| 12.5 | 70 | 112 | 118 | 107.4 | 102 | 50.2 | 1.63 | 1.0 | 0.177 |
| 55 | 74 | 108 | 109.4 | 109.3 | 100 | 50 | 3.28 | 2.0 | 0.075 |
| 79 | 87 | 119 | 116.8 | 116.2 | 110 | 51 | 3.27 | 2.0 | 0.061 |
| 103 | 88 | 118 | 118.1 | 117.4 | 110 | 50.2 | 4.9 | 3.0 | 0.065 |
| 120 | 87 | 120 | 118.1 | 116.5 | 110 | 49 | 1.63 | 1.0 | 0.088 |
| 143 | 73 | 96 | 97.4 | 96.3 | 91 | 49.8 | 1.63 | 1.0 | 0.104 |
| 159 | 79 | 103 | 102.7 | 101.8 | 97 | 50.1 | 1.63 | 1.0 | 0.045 |
| 168 | 71 | 109 | 110.9 | 109.2 | 100 | 50.1 | 1.63 | 1.0 | 0.068 |
| 182 | 82 | 123 | 120.6 | 118.2 | 111 | 49.9 | 1.64 | 1.0 | 0.068 |
| 208.5 | 78 | 122 | 124.3 | 122.8 | 112 | 50 | 2.05 | 1.25 | 0.065 |
| 256 | 82 | 128 | 130.8 | 128.9 | 117 | 100.1 | 2.06 | 1.26 | 0.097 |
| 270 | 77 | 124 | 133.7 | 130.3 | 116 | 99.9 | 2.46 | 1.50 | 0.071 |
| 306 | 82 | 128 | 139.7 | 138.7 | 122 | 99.9 | 2.85 | 1.74 | 0.133 |
| 325 | 88 | 139 | 149.9 | 148.9 | 131 | 100.2 | 2.86 | 1.74 | 0.125 |
| 353 | 89 | 143 | 154 | 152.8 | 135 | 100.1 | 2.85 | 1.74 | 0.118 |
| 375 | 99 | 148 | 148 | 148 | 136 | 100 | 2.85 | 1.74 | 0.115 |
| 399 | 102 | 155 | 155.2 | 155.2 | 142 | 100.2 | 2.83 | 1.73 | 0.139 |
| 424 | 106 | 161 | 158.7 | 157.6 | 146 | 100.2 | 2.85 | 1.74 | 0.141 |
| 451 | 109 | 164 | 160.9 | 159.3 | 148 | 99.9 | 2.92 | 1.78 | 0.107 |
| 458 | 109 | 167 | 165.4 | 164.8 | 152 | 100 | 2.83 | 1.73 | 0.162 |
| 475 | 108 | 168 | 168.7 | 168.8 | 153 | 100 | 2.80 | 1.71 | 0.179 |
| 497 | 108 | 168 | 171.4 | 171.3 | 155 | 100.4 | 2.82 | 1.72 | 0.080 |
| 525 | 109 | 168 | 170.4 | 170.2 | 154 | 100.6 | 2.81 | 1.71 | 0.185 |
| 551 | 107 | 168 | 170.7 | 170.2 | 154 | 100.5 | 2.82 | 1.72 | 0.178 |
| 572 | 108 | 167 | 170.7 | 170.3 | 154 | 99.8 | 2.85 | 1.74 | 0.163 |
| 603 | 94 | 158 | 186.1 | 186.6 | 156 | 99.8 | 2.86 | 1.74 | 0.383 |
| 626 | 91 | 147 | 175.7 | 172.3 | 147 | 99.9 | 2.85 | 1.74 | 0.185 |
| 650 | 91 | 149 | 178.5 | 174.3 | 148 | 99.5 | 2.87 | 1.75 | 0.180 |
| 674 | 95 | 155 | 183.4 | 179.1 | 153 | 100.1 | 2.86 | 1.74 | 0.209 |
| 699 | 92 | 151 | 181.4 | 177.5 | 150 | 100 | 2.86 | 1.74 | 0.131 |
| 726 | 116.7 | 165.2 | 165.4 | 167.4 | 154 | 100.2 | 2.83 | 1.73 | 0.120 |
| 749 | 114.7 | 175.1 | 175.3 | 175.4 | 160 | 100.2 | 2.84 | 1.73 | 0.173 |
| 775 | 116.9 | 178.1 | 179.3 | 179.5 | 163 | 99.7 | 2.85 | 1.74 | 0.165 |
| 802 | 117.6 | 185.1 | 185.6 | 186 | 169 | 100.6 | 2.85 | 1.74 | 0.217 |
| 825 | 108.1 | 161.7 | 159.5 | 169.7 | 150 | 99.9 | 2.85 | 1.74 | 0.103 |
| 850 | 121.1 | 179.1 | 177.2 | 181.6 | 165 | 100.1 | 2.84 | 1.73 | 0.160 |
| 873 | 132 | 184.7 | 183.4 | 185.6 | 171 | 100 | 2.85 | 1.74 | 0.074 |
| 900 | 136.3 | 186.1 | 184.9 | 186.5 | 173 | 100.3 | 2.83 | 1.73 | 0.177 |
| 925 | 122.5 | 189.5 | 195.3 | 188.8 | 174 | 99.8 | 2.85 | 1.74 | 0.280 |
| 951 | 108.8 | 181.6 | 187 | 187.8 | 166 | 100.1 | 2.85 | 1.74 | 0.183 |
| 974 | 124.2 | 188.3 | 189.3 | 191.3 | 173 | 99.9 | 2.85 | 1.74 | 0.216 |
| 981 | 125.4 | 188.6 | 187.1 | 187.9 | 172 | 100 | 2.85 | 1.74 | 0.182 |

TABLE XI-continued

Reactor Effluent Analyses

| Hours On-line | t-1,2-DMCP (wt %) | n-heptane (wt %) | c-1,2-DMCP (wt %) | MCH (wt %) | c-1,2-DMCP % remvd | n-heptane Δ wt % | Br Index (mgBr/100 g) |
|---|---|---|---|---|---|---|---|
| 12.5 | 0.082 | 99.492 | 0 | 0.249 | 100 | 0.11 | |
| 55 | 0.099 | 99.591 | 0.086 | 0.149 | 82 | 0.21 | |
| 79 | 0.114 | 99.585 | 0.08 | 0.16 | 83 | 0.20 | |
| 103 | 0.086 | 99.543 | 0.175 | 0.131 | 63 | 0.16 | |
| 120 | 0.103 | 99.577 | 0.065 | 0.166 | 86 | 0.20 | |
| 143 | 0.084 | 99.543 | 0.24 | 0.099 | 49 | 0.16 | |
| 159 | 0.083 | 99.571 | 0.187 | 0.114 | 60 | 0.19 | |
| 168 | 0.087 | 99.577 | 0.131 | 0.137 | 72 | 0.20 | |
| 182 | 0.114 | 99.578 | 0.076 | 0.165 | 84 | 0.20 | |
| 208.5 | 0.107 | 99.553 | 0.093 | 0.166 | 80 | 0.17 | |
| 256 | 0.103 | 99.542 | 0.088 | 0.17 | 81 | 0.16 | |
| 270 | 0.104 | 99.543 | 0.112 | 0.17 | 76 | 0.16 | |
| 306 | 0.112 | 99.526 | 0.116 | 0.171 | 75 | 0.15 | |
| 325 | 0.100 | 99.491 | 0.083 | 0.198 | 82 | 0.11 | |
| 353 | 0.113 | 99.482 | 0.081 | 0.206 | 83 | 0.10 | |
| 375 | 0.088 | 99.511 | 0.102 | 0.184 | 78 | 0.13 | |
| 399 | 0.099 | 99.478 | 0.08 | 0.205 | 83 | 0.10 | |
| 424 | 0.102 | 99.466 | 0.089 | 0.202 | 81 | 0.08 | 15.1 |
| 451 | 0.108 | 99.464 | 0.11 | 0.196 | 77 | 0.08 | |
| 458 | 0.092 | 99.43 | 0.084 | 0.217 | 82 | 0.05 | |
| 475 | 0.096 | 99.423 | 0.073 | 0.229 | 85 | 0.04 | |
| 497 | 0.092 | 99.53 | 0.053 | 0.246 | 89 | 0.15 | |
| 525 | 0.096 | 99.42 | 0.056 | 0.242 | 88 | 0.04 | |
| 551 | 0.100 | 99.423 | 0.065 | 0.234 | 86 | 0.04 | 16.9 |
| 572 | 0.094 | 99.439 | 0.079 | 0.225 | 83 | 0.06 | |
| 603 | 0.082 | 99.223 | 0.022 | 0.29 | 95 | −0.16 | |
| 626 | 0.097 | 99.412 | 0.068 | 0.238 | 86 | 0.03 | |
| 650 | 0.096 | 99.409 | 0.085 | 0.23 | 82 | 0.03 | |
| 674 | 0.095 | 99.382 | 0.069 | 0.244 | 85 | 0.00 | |
| 699 | 0.070 | 99.449 | 0.287 | 0.117 | 39 | 0.07 | |
| 726 | 0.104 | 99.471 | 0.093 | 0.212 | 80 | 0.09 | |
| 749 | 0.095 | 99.425 | 0.078 | 0.229 | 83 | 0.04 | |
| 775 | 0.093 | 99.424 | 0.098 | 0.219 | 79 | 0.04 | |
| 802 | 0.093 | 99.379 | 0.064 | 0.247 | 86 | 0.00 | |
| 825 | 0.103 | 99.439 | 0.172 | 0.182 | 63 | 0.06 | 21.4 |
| 850 | 0.093 | 99.429 | 0.091 | 0.227 | 81 | 0.05 | |
| 873 | 0.086 | 99.521 | 0.084 | 0.236 | 82 | 0.14 | |
| 900 | 0.090 | 99.412 | 0.089 | 0.232 | 81 | 0.03 | 21.3 |
| 925 | 0.095 | 99.335 | 0.03 | 0.261 | 94 | −0.05 | |
| 951 | 0.096 | 99.404 | 0.082 | 0.235 | 83 | 0.02 | |
| 974 | 0.086 | 99.404 | 0.052 | 0.242 | 89 | 0.02 | |
| 981 | 0.101 | 99.421 | 0.071 | 0.275 | 85 | 0.04 | 22.1 |

At the conclusion of the run, the spent catalyst was removed from the top, middle, and bottom of the catalyst bed and analyzed for coke deposition. The results are shown in Table XII. In this example, the catalyst had lost about 70 degrees Celsius of activity, and it had accumulated about 6 weight percent coke. Therefore, each incremental 1 weight percent of coke deposition approximately corresponded to about 11 degrees Celsius of catalyst deactivation.

The Bromine Index (defined as milligrams of Br necessary to titrate 100 grams of sample) was also measured and reported in Tables X and XI. Bromine Index is a measure of olefin content. The results show that the olefin content, as measured by Bromine Index, was reduced from about 40 in the feed to about 15 to 22 in the reactor effluent for the duration of the run.

TABLE XII

Spent Catalyst Analyses

| Location | Example No. | C (wt %) | H (wt %) |
|---|---|---|---|
| Top | 7 | 4.81 | 1.96 |
| Middle | 7 | 6.54 | 1.92 |
| Bottom | 7 | 10.42 | 2.14 |
| Top | 8 | 2.83 | 2.21 |
| Middle | 8 | 4.84 | 2.24 |
| Bottom | 8 | 11.41 | 2.28 |

Example 8

This experiment had a duration of about 400 hours on-stream. Data from analyses of the reactor feed are shown in Table XIII, and data from the reactor effluent are shown in Table XIV. Temperature (WAT) was raised in response to catalyst deactivation in order to keep the cis-1,2-DMCP concentration in the reactor effluent at 0.085 weight percent. No attempts were made to regenerate the catalyst by burning off the coke at the end of the run.

TABLE XIII

Reactor Feed Analyses

| On-line Time (hours) | t-1,2-DMCP (wt %) | n-heptane (wt %) | Misc. (wt %) | c-1,2-DMCP (wt %) | MCH (wt %) | Br Index (mgBr/100 gms) |
|---|---|---|---|---|---|---|
| 8 | 0.034 | 99.39 | 0.02 | 0.472 | 0.061 | |
| 26 | 0.033 | 99.357 | 0.053 | 0.475 | 0.06 | 38.7 |
| 107 | 0.033 | 99.36 | 0.049 | 0.476 | 0.06 | |
| 171 | 0.032 | 99.36 | 0.049 | 0.477 | 0.058 | |
| 314 | 0.035 | 99.373 | 0.036 | 0.471 | 0.063 | |

TABLE XIV

Reactor Effluent Analyses

| Hours On-line | Top T (° C.) | Middle Temp. (° C.) | Middle Temp. (° C.) | Bottom Temp. (° C.) | WAT (° C.) | Pressure (psig) | Feed rate (lb/hr) | WHSV (hr$^{-1}$) | Lights (wt %) |
|---|---|---|---|---|---|---|---|---|---|
| 1 | 76.1 | 98.2 | 98.1 | 90.8 | 91 | 100.0 | 2.86 | 1.74 | 0.081 |
| 25 | 102.5 | 119.1 | 120.2 | 118 | 115 | 99.7 | 2.87 | 1.75 | 0.138 |
| 54 | 105.7 | 119.8 | 120.4 | 119 | 116 | 99.9 | 2.85 | 1.74 | 0.121 |
| 79 | 104.6 | 119.4 | 120.1 | 118 | 116 | 99.9 | 2.84 | 1.73 | 0.087 |
| 103 | 102.7 | 118.8 | 119.9 | 118 | 115 | 100.0 | 2.85 | 1.74 | 0.097 |
| 127 | 105.7 | 119.5 | 119.8 | 118 | 116 | 99.9 | 2.85 | 1.74 | 0.088 |
| 148 | 107.1 | 125.6 | 124.1 | 122 | 120 | 99.8 | 2.88 | 1.76 | 0.085 |
| 172 | 107.2 | 126.9 | 125 | 123 | 121 | 99.6 | 2.86 | 1.74 | 0.029 |
| 199 | 115.6 | 131.9 | 128.3 | 126 | 126 | 99.9 | 2.85 | 1.74 | 0.090 |
| 224 | 108.1 | 131.9 | 130.6 | 129 | 125 | 100.0 | 2.86 | 1.74 | 0.094 |
| 250 | 106.5 | 134.6 | 133.5 | 132 | 127 | 100.0 | 2.85 | 1.74 | 0.074 |
| 275 | 116.4 | 138.6 | 135.1 | 133 | 131 | 100.0 | 2.85 | 1.74 | 0.073 |
| 302 | 121 | 141.5 | 138.1 | 137 | 134 | 100.0 | 2.85 | 1.74 | 0.076 |
| 328 | 123.1 | 142.4 | 140.3 | 140 | 137 | 100.3 | 2.84 | 1.73 | 0.112 |
| 358 | 119.8 | 146.2 | 140.8 | 138.9 | 136 | 101.2 | 2.84 | 1.73 | 0.110 |
| 367 | 122.9 | 142.2 | 139.9 | 140 | 136 | 100.1 | 2.86 | 1.74 | 0.102 |
| 376 | 125.7 | 143.8 | 141.2 | 141.2 | 138 | 100.3 | 2.85 | 1.74 | 0.103 |
| 388 | 126.2 | 144.1 | 141.6 | 141.3 | 138 | 100 | 2.85 | 1.74 | 0.098 |

| Hours On-line | t-1,2-DMCP (wt %) | n-heptane (wt %) | c-1,2-DMCP (wt %) | MCH (wt %) | c-1,2-DMCP % remvd | n-heptane Δ wt % | Br Index (mgBr/100 g) |
|---|---|---|---|---|---|---|---|
| 1 | 0.106 | 99.615 | 0.05 | 0.147 | 89 | 0.23 | |
| 25 | 0.096 | 99.526 | 0.019 | 0.222 | 96 | 0.15 | 19.9 |
| 54 | 0.101 | 99.547 | 0.026 | 0.205 | 94 | 0.17 | |
| 79 | 0.105 | 99.58 | 0.038 | 0.19 | 92 | 0.20 | |
| 103 | 0.107 | 99.566 | 0.051 | 0.178 | 89 | 0.19 | 21.6 |
| 127 | 0.105 | 99.568 | 0.074 | 0.165 | 84 | 0.19 | |
| 148 | 0.095 | 99.567 | 0.083 | 0.17 | 82 | 0.19 | |
| 172 | 0.037 | 99.679 | 0.086 | 0.17 | 82 | 0.30 | |
| 199 | 0.102 | 99.547 | 0.091 | 0.169 | 81 | 0.17 | |
| 224 | 0.107 | 99.539 | 0.084 | 0.176 | 82 | 0.16 | |
| 250 | 0.112 | 99.553 | 0.082 | 0.18 | 83 | 0.17 | |
| 275 | 0.111 | 99.547 | 0.092 | 0.177 | 80 | 0.17 | |
| 302 | 0.021 | 99.633 | 0.09 | 0.18 | 81 | 0.25 | |
| 328 | 0.107 | 99.519 | 0.061 | 0.2 | 87 | 0.14 | |
| 358 | 0.106 | 99.525 | 0.061 | 0.197 | 87 | 0.14 | |
| 367 | 0.102 | 99.527 | 0.083 | 0.185 | 82 | 0.15 | |
| 376 | 0.104 | 99.524 | 0.087 | 0.183 | 82 | 0.14 | 17.1 |
| 388 | 0.103 | 99.525 | 0.098 | 0.176 | 79 | 0.14 | |

At the conclusion of the run, the spent catalyst was removed from the top, middle, and bottom of the catalyst bed and analyzed for coke deposition. The results are shown above in Table XII. The loss in activity during the test in Example 8 was about 5 degrees Celsius per 1 weight percent coke. Fresh catalyst has 0 weight percent carbon.

The Bromine Index was also measured and reported. The results show that the olefin content, as measured by Bromine Index, was reduced from about 38 to 40 in the feed to about 17 to 22 in the reactor effluent for the duration of the run.

A detailed GC analysis of a composite sample of the heptane product from the test in Example 8 is shown below in Table XV. The data in Table XV shows the reduction of about 80 to 90 weight percent of the cis-1,2-DMCP in the product heptane.

TABLE XV

Reactor Aggregate Product Heptane Analysis From Example 8

| compound | BP (° F.) | BP (° C.) | Time (min.) | Area Counts | Area % |
|---|---|---|---|---|---|
| light (BP < 165 F.) | | | 0.792 | 40.60 | 0.001 |
| light (BP < 165 F.) | | | 1.715 | 78.90 | 0.003 |
| light (BP < 165 F.) | | | 4.436 | 30.30 | 0.001 |
| light (BP < 165 F.) | | | 6.15 | 109.74 | 0.004 |
| light (BP < 165 F.) | | | 6.431 | 21.96 | 0.001 |
| light (BP < 165 F.) | | | 7.454 | 53.70 | 0.002 |
| Acetone, ignore | | | 7.497 | 1346.4 | 0.000 |
| light (BP < 165 F.) | | | 9.015 | 40.50 | 0.001 |
| light (BP < 165 F.) | | | 10.322 | 44.50 | 0.002 |
| light (BP < 165 F.) | | | 13.905 | 164.30 | 0.006 |
| light (BP < 165 F.) | | | 14.862 | 38.00 | 0.001 |
| 1,1-dimethylcyclopentane | 190.1 | 87.8 | 17.531 | 47.10 | 0.002 |
| 2,3-dimethylpentane | 193.6 | 89.8 | 17.285 | 243.47 | 0.009 |
| 2-methylhexane | 194.1 | 90.1 | 17.09 | 1382.23 | 0.049 |
| cis-1,3-dimethylcyclopentane | 195.4 | 90.8 | 18.624 | 1978.65 | 0.070 |
| trans-1,3-dimethylcyclopentane | 197.1 | 91.7 | 18.926 | 1732.24 | 0.061 |
| 3-methylhexane | 197.3 | 91.8 | 17.966 | 1460.30 | 0.051 |
| trans-1,2-dimethylcyclopentane | 197.4 | 91.9 | 19.215 | 2874.25 | 0.101 |
| 3-ethylpentane | 200.3 | 93.5 | 19.068 | 589.56 | 0.021 |
| unidentified | ~205 | 96.1 | 20.175 | 19.95 | 0.001 |
| n-heptane | 209.2 | 98.4 | 21.014 | 2820757.45 | 99.306 |
| Isooctane (2,2,4-trimethylpentane) | 210.3 | 99.1 | 19.436 | 734.55 | 0.026 |
| cis-1,2-dimethylcyclopentane | 211.2 | 99.6 | 23.103 | 2201.00 | 0.077 |
| methylcyclohexane | 213.7 | 100.9 | 23.204 | 5562.60 | 0.196 |
| ethylcyclopentane | 218.2 | 103.4 | 24.888 | 147.60 | 0.005 |
| toluene | 231.1 | 110.6 | 28.4 | 30.20 | 0.001 |
| heavy (BP > 230 F.) | | | 38.513 | 80.00 | 0.003 |
| total | | | | 2840463.65 | 100.00 |

Example 9

459 gallons of the reactor effluent from Example 8 was supplied to a fractionator. The feed to the fractionator possessed an average purity of 99.464 weight percent n-heptane and 0.082 weight percent cis-1,2-DMCP. Results of the fractionation are shown in Table XVI. The run produced 288 gallons of PRF n-heptane with an average purity of 99.757 weight percent n-heptane and 0.032 weight percent cis-1,2-DMCP. The fractionation was run at about 5 psig. The kettle temperature was about 93 to 99° C. The column was run at 110 inches $H_2O$ $\Delta p$ (about 95 percent of flood point). Overhead rate varied between 10 and 20 pounds per hour. Running at higher pressure makes the cut easier. The distillation was performed over a period of 13 days. The column overhead was sampled every four to six hours and analyzed using a gas chromatograph using a boiling point column. Thus, order of dilution is from lowest to highest boiling component.

TABLE XVI

Isomerized Heptane Fractionation at 5 psig (Component Concentration (wt. %))

| Sample Date (Time) | 2-Methyl-hexane | 3-Methyl-hexane | cis-1,3-Dimethyl-cyclopentane | trans-1,3-Dimethyl-cyclopentane | 3-Ethyl-pentane | trans-1,2-Dimethyl-cyclopentane | Isooctane |
|---|---|---|---|---|---|---|---|
| 6/12/02 (11:54 AM) | 0.474 | 0.689 | 0.812 | 0.861 | 0.384 | 1.49 | 0.009 |
| 6/13/02 (11:00 AM) | 0.083 | 0.132 | 0.145 | 0.159 | 0.077 | 0.277 | 0.027 |
| 6/13/02 (4:48 PM) | 0.046 | 0.084 | 0.086 | 0.102 | 0.058 | 0.181 | 0.023 |
| 6/13/02 (9:51 PM) | 0.008 | 0.018 | 0.017 | 0.022 | 0.017 | 0.041 | 0.027 |
| 6/14/02 (1:45 AM) | 0 | 0.008 | 0.006 | 0.009 | 0.008 | 0.017 | 0.025 |
| 6/14/02 (6:51 AM) | 0 | 0.004 | 0.003 | 0.006 | 0.006 | 0.01 | 0.025 |
| 6/19/02 (1:08 PM) | 1.129 | 1.147 | 1.567 | 1.392 | 0.421 | 2.272 | 0.002 |
| 6/19/02 (6:23 PM) | 0.194 | 0.243 | 0.298 | 0.294 | 0.115 | 0.494 | 0.002 |
| 6/19/02 (9:46 PM) | 0.046 | 0.071 | 0.078 | 0.085 | 0.04 | 0.146 | 0.009 |
| 6/20/02 (12:53 AM) | 0.027 | 0.049 | 0.052 | 0.059 | 0.03 | 0.105 | 0.013 |

TABLE XVI-continued

Isomerized Heptane Fractionation at 5 psig (Component Concentration (wt. %))

| | | | | | | | |
|---|---|---|---|---|---|---|---|
| 6/20/02 (4:11 AM) | 0.023 | 0.041 | 0.044 | 0.051 | 0.028 | 0.09 | 0.015 |
| 6/20/02 (8:07 AM) | 0.018 | 0.035 | 0.036 | 0.043 | 0.024 | 0.077 | 0.014 |
| 6/20/02 (12:33 PM) | 0.014 | 0.029 | 0.029 | 0.037 | 0.022 | 0.066 | 0.014 |
| 6/20/02 (7:34 PM) | 0.008 | 0.015 | 0.014 | 0.019 | 0.013 | 0.035 | 0.021 |
| 6/21/02 (1:28 AM) | 0.002 | 0.006 | 0.005 | 0.006 | 0 | 0.014 | 0.024 |
| 6/21/02 (4:50 AM) | 0.001 | 0.005 | 0.006 | 0.007 | 0 | 0.012 | 0.024 |
| 6/21/02 (7:01 AM) | 0.003 | 0.006 | 0.006 | 0.008 | 0.005 | 0.013 | 0.026 |
| 6/21/02 (12:36 PM) | 0 | 0.003 | 0.004 | 0.003 | 0 | 0.009 | 0.028 |
| 6/21/02 (5:59 PM) | 0.002 | 0.002 | 0.003 | 0.005 | 0.004 | 0.008 | 0.03 |
| 6/21/02 (10:07 PM) | 0 | 0 | 0 | 0 | 0 | 0.002 | 0.032 |
| 6/22/02 (1:45 AM) | 0 | 0 | 0 | 0.002 | 0 | 0.004 | 0.037 |
| 6/22/02 (8:21 AM) | 0 | 0 | 0 | 0 | 0 | 0 | 0.037 |
| 6/22/02 (1:02 PM) | 0 | 0 | 0 | 0 | 0 | 0 | 0.04 |
| 6/22/02 (6:00 PM) | 0 | 0 | 0 | 0 | 0 | 0.002 | 0.04 |
| 6/23/02 (2:32 AM) | 0 | 0.003 | 0 | 0.002 | 0 | 0 | 0.042 |
| 6/23/02 (2:32 AM) | 0 | 0 | 0 | 0 | 0 | 0 | 0.044 |
| 6/23/02 (6:28 AM) | 0 | 0 | 0 | 0 | 0 | 0 | 0.048 |
| 6/23/02 (12:48 PM) | 0 | 0 | 0.002 | 0 | 0 | 0.003 | 0.051 |
| 6/23/02 (10:19 PM) | 0.029 | 0.026 | 0.037 | 0.032 | 0.007 | 0.048 | 0.048 |
| 6/24/02 (1:52 AM) | 0 | 0 | 0 | 0 | 0 | 0 | 0.045 |
| 6/24/02 (10:36 AM) | 0 | 0 | 0 | 0 | 0 | 0 | 0.05 |
| 6/24/02 (2:10 PM) | 0 | 0 | 0 | 0 | 0 | 0 | 0.05 |

| Sample Date (Time) | n-Heptane | C7 | cis-1,2-Dimethyl-cyclopentane | Methyl-cyclohexane | cis,cis-1,2,3-Trimethyl-cyclopentane | Toluene | Others |
|---|---|---|---|---|---|---|---|
| 6/12/02 (11:54 AM) | 94.894 | 0 | 0 | 0.018 | 0.002 | 0 | 0.367 |
| 6/13/02 (11:00 AM) | 98.976 | 0 | 0.048 | 0.022 | 0 | 0 | 0.054 |
| 6/13/02 (4:48 PM) | 99.349 | 0 | 0.033 | 0 | 0 | 0 | 0.038 |
| 6/13/02 (9:51 PM) | 99.788 | 0 | 0.035 | 0 | 0 | 0 | 0.027 |
| 6/14/02 (1:45 AM) | 99.871 | 0 | 0.038 | 0 | 0 | 0 | 0.018 |
| 6/14/02 (6:51 AM) | 99.885 | 0 | 0.042 | 0 | 0 | 0 | 0.019 |
| 6/19/02 (1:08 PM) | 91.591 | 0 | 0 | 0.013 | 0 | 0.001 | 0.465 |
| 6/19/02 (6:23 PM) | 98.28 | 0 | 0 | 0.013 | 0 | 0 | 0.067 |
| 6/19/02 (9:46 PM) | 99.479 | 0 | 0.018 | 0 | 0 | 0 | 0.028 |
| 6/20/02 (12:53 AM) | 99.618 | 0 | 0.025 | 0 | 0 | 0 | 0.022 |
| 6/20/02 (4:11 AM) | 99.655 | 0 | 0.026 | 0 | 0 | 0 | 0.027 |
| 6/20/02 (8:07 AM) | 99.697 | 0 | 0.028 | 0 | 0 | 0 | 0.028 |

TABLE XVI-continued

Isomerized Heptane Fractionation at 5 psig (Component Concentration (wt. %))

| Date (Time) | | | | | | | |
|---|---|---|---|---|---|---|---|
| 6/20/02 (12:33 PM) | 99.708 | 0 | 0.028 | 0 | 0 | 0 | 0.053 |
| 6/20/02 (7:34 PM) | 99.827 | 0 | 0.035 | 0 | 0 | 0 | 0.013 |
| 6/21/02 (1:28 AM) | 99.863 | 0 | 0.057 | 0 | 0 | 0 | 0.023 |
| 6/21/02 (4:50 AM) | 99.869 | 0 | 0.042 | 0 | 0 | 0 | 0.034 |
| 6/21/02 (7:01 AM) | 99.839 | 0 | 0.057 | 0.014 | 0 | 0.001 | 0.022 |
| 6/21/02 (12:36 PM) | 99.858 | 0 | 0.057 | 0.015 | 0.001 | 0 | 0.022 |
| 6/21/02 (5:59 PM) | 99.874 | 0 | 0.048 | 0 | 0 | 0 | 0.024 |
| 6/21/02 (10:07 PM) | 99.839 | 0 | 0 | 0.07 | 0 | 0.001 | 0.056 |
| 6/22/02 (1:45 AM) | 99.848 | 0 | 0.071 | 0.023 | 0 | 0 | 0.015 |
| 6/22/02 (8:21 AM) | 99.839 | 0 | 0.076 | 0.032 | 0 | 0 | 0.016 |
| 6/22/02 (1:02 PM) | 99.82 | 0 | 0 | 0.078 | 0 | 0 | 0.062 |
| 6/22/02 (6:00 PM) | 99.816 | 0 | 0 | 0.083 | 0 | 0.001 | 0.058 |
| 6/23/02 (2:32 AM) | 99.788 | 0 | 0.041 | 0 | 0 | 0.001 | 0.123 |
| 6/23/02 (2:32 AM) | 99.805 | 0 | 0.09 | 0.047 | 0 | 0 | 0.014 |
| 6/23/02 (6:28 AM) | 99.716 | 0 | 0.107 | 0.119 | 0 | 0 | 0.01 |
| 6/23/02 (12:48 PM) | 99.766 | 0 | 0 | 0.099 | 0 | 0 | 0.079 |
| 6/23/02 (10:19 PM) | 99.594 | 0 | 0.097 | 0.04 | 0.001 | 0.001 | 0.04 |
| 6/24/02 (1:52 AM) | 99.866 | 0 | 0.001 | 0.068 | 0 | 0.001 | 0.019 |
| 6/24/02 (10:36 AM) | 99.769 | 0 | 0.099 | 0.065 | 0 | 0.001 | 0.016 |
| 6/24/02 (2:10 PM) | 99.679 | 0 | 0 | 0.116 | 0.001 | 0 | 0.154 |

Example 10

An n-heptane feed was subjected to an isomerization reaction in an effort to reduce the concentration of close boiling impurities. The isomerized product was then purified via fractionation. The reactor for the isomerization was a portable dryer that was 9 feet long and 12 inches in diameter. The catalyst was UOP LZY-84, 1/16 inch extrudate. Approximately 250 pounds of the catalyst was employed in the dryer. The heptane feed was rolled over a 4A molecular sieve for drying. The feed was preheated to 93.3 degrees Celsius and fed through the reactor with an outlet temperature from 71.1 degrees Celsius to 87.8 degrees Celsius. The reactor product was circulated back to the feed tank (reactor operated like recirculation reactor). Table XVII contains data showing the inlet and outlet component concentrations for the reactor.

TABLE XVII

Inlet and Outlet Component Concentrations Over Time for Recirculation Reactor

| Sample Date (Time) | | 2-Methyl-hexane | 3-Methyl-hexane | cis-1,3-Dimethyl-cyclopentane | trans-1,3-Dimethyl-cyclopentane | 3-Ethyl-pentane | trans-1,2-Dimethyl-cyclopentane | Isooctane | n-Heptane |
|---|---|---|---|---|---|---|---|---|---|
| 7/30/03 (11:59PM) | Feed | 0.015 | 0.032 | 0.026 | 0.067 | 0 | 0.091 | 0 | 99.136 |
| | Effluent | 0.014 | 0.035 | 0.034 | 0.067 | 0 | 0.103 | 0.047 | 99.187 |
| 7/31/03 (7:35 AM) | Feed | 0.016 | 0.036 | 0.037 | 0.067 | 0 | 0.108 | 0.047 | 99.143 |
| | Effluent | 0.017 | 0.036 | 0.043 | 0.066 | 0 | 0.114 | 0.046 | 99.16 |
| 8/1/03 (1:17 AM) | Feed | 0.023 | 0.043 | 0.056 | 0.064 | 0 | 0.13 | 0.043 | 99.151 |
| | Effluent | 0.024 | 0.044 | 0.057 | 0.065 | 0 | 0.138 | 0.052 | 99.171 |
| 8/2/03 (0:51 AM) | Feed | 0.028 | 0.047 | 0.064 | 0.063 | 0 | 0.148 | 0.046 | 99.136 |
| | Effluent | 0.029 | 0.046 | 0.065 | 0.063 | 0 | 0.148 | 0.045 | 99.191 |

TABLE XVII-continued

Inlet and Outlet Component Concentrations Over Time for Recirculation Reactor

| Sample Date (Time) | | C7 | cis-1,2-Dimethyl-cyclopentane | Methyl-cyclohexane | cis,cis-1,2,3-Trimethyl-cyclopentane | Toluene | Others | Bromine Number |
|---|---|---|---|---|---|---|---|---|
| 7/30/03 | Feed | 0 | 0.284 | 0.069 | 0.001 | 0.001 | 0.278 | |
| (11:59PM) | Effluent | 0 | 0.239 | 0.077 | 0.001 | 0.002 | 0.194 | |
| 7/31/03 | Feed | 0 | 0.221 | 0.082 | 0 | 0 | 0.243 | 0.002 |
| (7:35 AM) | Effluent | 0 | 0.196 | 0.088 | 0.001 | 0.001 | 0.232 | 0.008 |
| 8/1/03 | Feed | 0 | 0.123 | 0.107 | 0.001 | 0.002 | 0.257 | |
| (1:17 AM) | Effluent | 0 | 0.114 | 0.111 | 0.002 | 0.001 | 0.221 | |
| 8/2/03 | Feed | 0 | 0.07 | 0.121 | 0.001 | 0.002 | 0.274 | |
| (0:51 AM) | Effluent | 0 | 0.065 | 0.126 | 0.001 | 0.004 | 0.217 | |

The reactor effluent recorded in Table XVII was subsequently fed to a fractionator. The fractionator was 68 feet tall, 10 inches in diameter, and packed with ½" steel Pall rings. These factors would typically correspond to a fractionator with about 45 stages. Table XVIII shows the equipment/process settings for the fractionation and the results of the fractionation. The data show that the concentration of n-heptane in the product stream is capable of exceeding 99.9 weight percent.

TABLE XVIII

Fractionation Settings and Fractionation Product Results in Weight Percent

| Date (Time) | Kettle Temp. (° F.) | Top Temp. (° F.) | Column Pressure (psig) | Differential Pressure (psi) | Overhead Flowrate (units) | n-Heptane | 2-Methyl Hexane | 3-Methyl Hexane | Cis-1,3-Dimethyl-cyclopentane | trans-1,3-Dimethyl-cyclopentane |
|---|---|---|---|---|---|---|---|---|---|---|
| 7/25/03 (8:41) | | | | | | 99.175 | 0 | 0.043 | 0.009 | 0.11 |
| 7/25/03 (10:10) | 290.8 | 81.7 | 36.9 | −0.6 | 0.2 | 99.074 | 0.002 | 0.038 | 0.011 | 0.104 |
| 7/25/03 (14:03) | 287.5 | 88.1 | 32.7 | 0.4 | 2.8 | 98.753 | 0.004 | 0.041 | 0.016 | 0.108 |
| 7/25/03 (18:13) | 263.3 | 111.5 | 20.6 | 3.4 | 22.9 | 98.377 | 0.086 | 0.102 | 0.119 | 0.101 |
| 7/26/03 (0:10) | 250.5 | 126.6 | 14.8 | 2.8 | 22.6 | 98.828 | 0.078 | 0.096 | 0.112 | 0.097 |
| 7/26/03 (8:39) | 250.0 | 141.5 | 14.2 | 2.9 | 23.0 | 98.58 | 0.113 | 0.13 | 0.155 | 0.129 |
| 7/26/03 (13:57) | 250.0 | 151.1 | 14.1 | 3.4 | 24.5 | 98.725 | 0.116 | 0.135 | 0.162 | 0.138 |
| 7/26/03 (18:02) | 250.0 | 155.8 | 14.4 | 3.6 | 24.3 | 98.756 | 0.113 | 0.134 | 0.162 | 0.136 |
| 7/26/03 (23:52) | 250.1 | 156.6 | 14.2 | 3.6 | 24.0 | 98.811 | 0.109 | 0.131 | 0.155 | 0.134 |
| 7/27/03 (7:53) | 250.0 | 156.2 | 14.1 | 3.7 | 24.3 | 98.889 | 0.1 | 0.124 | 0.147 | 0.127 |
| 7/27/03 (11:16) | 250.1 | 154.6 | 14.2 | 3.8 | 23.9 | 98.904 | 0.097 | 0.125 | 0.142 | 0.124 |
| 7/27/03 (18:07) | 250.1 | 158.7 | 14.5 | 3.8 | 23.5 | 99.046 | 0.081 | 0.108 | 0.124 | 0.11 |
| 7/27/03 (23:45) | 250.1 | 158.8 | 14.2 | 3.9 | 23.0 | 99.081 | 0.077 | 0.104 | 0.119 | 0.105 |
| 7/28/03 (6:30) | 250.0 | 159.5 | 14.0 | 3.9 | 23.1 | 99.116 | 0.071 | 0.095 | 0.11 | 0.095 |
| 7/28/03 (12:47) | 249.9 | 159.4 | 14.3 | 3.9 | 23.2 | 99.177 | 0.064 | 0.088 | 0.101 | 0.093 |
| 7/28/03 (18:09) | 250.1 | 163.3 | 14.7 | 3.9 | 21.6 | 99.26 | 0.055 | 0.077 | 0.09 | 0.081 |
| 7/28/03 (23:54) | 250.1 | 163.2 | 14.4 | 4.0 | 21.7 | 99.311 | 0.048 | 0.074 | 0.081 | 0.079 |
| 7/29/03 (6:31) | 250.1 | 164.0 | 14.1 | 3.9 | 21.6 | 99.355 | 0.043 | 0.066 | 0.075 | 0.072 |
| 7/30/03 (18:31) | 235.0 | 159.2 | 12.8 | 3.6 | 2.4 | 99.376 | 0.038 | 0.062 | 0.07 | 0.07 |
| 7/31/03 (14:27) | 250.0 | 161.1 | 14.1 | 4.1 | 0.1 | 99.358 | 0.041 | 0.067 | 0.075 | 0.075 |
| 7/31/03 (19:04) | 250.0 | 159.7 | 14.6 | 3.0 | 26.1 | 99.016 | 0.046 | 0.085 | 0.106 | 0.126 |
| 8/1/03 (7:36) | 250.1 | 125.6 | 14.4 | 1.6 | 23.4 | 99.075 | 0.029 | 0.053 | 0.085 | 0.079 |

TABLE XVIII-continued

Fractionation Settings and Fractionation Product Results in Weight Percent

| | | | | | | | | | | |
|---|---|---|---|---|---|---|---|---|---|---|
| 8/1/03 (13:04) | 250.1 | 110.7 | 14.9 | 1.5 | 3.7 | 98.641 | 0.044 | 0.074 | 0.12 | 0.102 |
| 8/1/03 (18:20) | 266.9 | 121.3 | 22.1 | 1.4 | 18.5 | 99.394 | 0.017 | 0.033 | 0.051 | 0.052 |
| 8/2/03 (0:02) | 270.0 | 138.4 | 23.4 | 1.8 | 47.8 | 99.552 | 0.003 | 0.01 | 0.008 | 0.01 |
| 8/2/03 (6:37) | 270.1 | 151.1 | 23.1 | 1.9 | 49.4 | 99.684 | 0.001 | 0.009 | 0.009 | 0.017 |
| 8/2/03 (12:05) | 270.0 | 155.5 | 23.5 | 2.0 | 20.6 | 99.763 | 0.005 | 0.01 | 0.012 | 0.013 |
| 8/2/03 (18:07) | 270.2 | 154.2 | 23.3 | 1.8 | 21.1 | 99.327 | 0.021 | 0.04 | 0.067 | 0.062 |
| 8/2/03 (23:52) | 270.3 | 125.5 | 23.2 | 1.2 | 11.5 | 98.546 | 0.053 | 0.086 | 0.137 | 0.116 |
| Start Batch Operation | | | | | | | | | | |
| 8/3/03 (6:16) | 270.2 | 111.8 | 23.0 | 0.8 | 2.0 | 51.27 | 0 | 0.298 | 1.75 | 5.753 |
| 8/3/03 (9:01) | 270.2 | 112.2 | 23.3 | 0.7 | 0.8 | 97.239 | 0.142 | 0.197 | 0.335 | 0.218 |
| 8/3/03 (15:07) | 271.2 | 173.9 | 23.0 | 23.3 | 7.9 | 98.685 | 0.064 | 0.117 | 0.193 | 0.17 |
| 8/3/03 (18:23) | 272.2 | 269.0 | 23.2 | 10.8 | 29.1 | 99.227 | 0.028 | 0.059 | 0.096 | 0.107 |
| 8/4/03 (0:09) | 272.3 | 197.9 | 23.4 | 2.4 | 25.6 | 99.408 | 0.019 | 0.001 | 0.06 | 0.144 |
| 8/4/03 (18:03) | 274.7 | 125.4 | 26.8 | 1.3 | 17.1 | 98.656 | 0.03 | 0.053 | 0.088 | 0.076 |
| 8/5/03 (18:22) | 246.2 | 130.9 | 12.8 | 7.1 | 12.7 | 97.867 | 0.128 | 0.198 | 0.358 | 0.256 |
| 8/6/03 (0:04) | 235.2 | 229.5 | 8.8 | 37.0 | 15.9 | 97.695 | 0.135 | 0.223 | 0.391 | 0.303 |
| 8/6/03 (5:39) | 235.3 | 229.0 | 8.4 | 48.3 | 17.3 | 97.014 | 0.175 | 0.296 | 0.52 | 0.405 |
| 8/6/03 (13:13) | 235.2 | 229.6 | 8.5 | 39.6 | 19.1 | 97.879 | 0.105 | 0.199 | 0.313 | 0.294 |
| 8/6/03 (18:31) | 235.1 | 179.4 | 9.5 | 3.8 | 23.1 | 98.92 | 0.054 | 0.089 | 0.124 | 0.11 |
| 8/7/03 (5:51) | 230.9 | 180.7 | 7.5 | 63.5 | 15.1 | 98.803 | 0.049 | 0.113 | 0.174 | 0.197 |
| Start New Batch | | | | | | | | | | |
| 8/8/03 (9:31) | 229.7 | 171.0 | 8.5 | 63.7 | 5.3 | 92.957 | 0.658 | 0.764 | 1.161 | 0.99 |
| 8/8/03 (18:16) | 224.8 | 208.7 | 6.0 | 101.4 | 9.5 | 95.913 | 0.365 | 0.45 | 0.657 | 0.582 |
| 8/8/03 (23:08) | 258.5 | 246.2 | 17.3 | 120.0 | 14.8 | 98.543 | 0.113 | 0.169 | 0.219 | 0.19 |
| 8/9/03 (6:18) | 254.4 | 242.6 | 16.2 | 120.0 | 1.0 | 98.676 | 0.102 | 0.152 | 0.196 | 0.173 |
| 8/9/03 (17:36) | 258.8 | 248.1 | 17.8 | 120.0 | 13.8 | 99.075 | 0.057 | 0.103 | 0.128 | 0.145 |
| 8/9/03 (23:27) | 262.9 | 253.0 | 19.4 | 120.0 | 18.8 | 99.46 | 0.029 | 0.057 | 0.068 | 0.084 |
| 8/10/03 (6:23) | 259.4 | 249.2 | 17.8 | 120.0 | 17.5 | 99.472 | 0.025 | 0.054 | 0.065 | 0.084 |
| 8/10/03 (11:42) | 259.2 | 248.9 | 18.0 | 120.0 | 20.3 | 99.723 | 0.011 | 0.026 | 0.028 | 0.043 |
| 8/10/03 (17:53) | 264.4 | 254.3 | 19.5 | 120.0 | 7.8 | 99.448 | 0.024 | 0.058 | 0.069 | 0.096 |
| 8/10/03 (23:42) | 262.9 | 252.9 | 19.9 | 120.0 | 6.5 | 99.337 | 0.026 | 0.068 | 0.08 | 0.121 |
| 8/11/03 (8:15) | 259.2 | 248.8 | 17.8 | 120.0 | 12.1 | 99.734 | 0.006 | 0.021 | 0.024 | 0.046 |
| 8/11/03 (12:36) | 261.1 | 250.9 | 18.8 | 119.9 | 35.8 | 99.884 | 0.001 | 0.007 | 0.007 | 0.017 |
| 8/11/03 (18:37) | 267.4 | 258.0 | 21.4 | 120.0 | 52.0 | 99.905 | 0.001 | 0.001 | 0.002 | 0.005 |
| 8/11/03 (23:11) | 269.4 | 259.7 | 21.8 | 120.0 | 63.9 | 99.938 | 0.001 | 0.005 | 0.006 | 0.013 |
| 8/12/03 (6:17) | 267.4 | 257.5 | 21.1 | 120.0 | 64.0 | 99.87 | 0.001 | 0 | 0.002 | 0.007 |
| 8/12/03 (11:24) | 267.5 | 257.9 | 21.3 | 120.0 | 89.6 | 99.83 | 0 | 0 | 0.001 | 0.003 |
| 8/12/03 (18:06) | 269.5 | 260.3 | 22.2 | 120.1 | 82.5 | 99.88 | 0 | 0 | 0 | 0 |

TABLE XVIII-continued

Fractionation Settings and Fractionation Product Results in Weight Percent

| | | | | | | | | | | |
|---|---|---|---|---|---|---|---|---|---|---|
| 8/13/03 (0:05) | 265.4 | 255.7 | 20.2 | 120.1 | 50.8 | 99.888 | 0.001 | 0.001 | 0.001 | 0.002 |
| 8/13/03 (5:45) | 261.2 | 251.0 | 18.4 | 120.0 | 51.4 | 99.89 | 0.001 | 0 | 0 | 0 |
| 8/13/03 (12:24) | 261.7 | 251.6 | 18.3 | 120.0 | 64.6 | 99.899 | 0 | 0.001 | 0 | 0.031 |
| 8/13/03 (18:46) | 268.3 | 258.9 | 21.4 | 120.0 | 64.8 | 99.876 | 0 | 0 | 0 | 0 |
| 8/13/03 (23:52) | 268.7 | 259.0 | 21.6 | 120.1 | 65.2 | 99.816 | 0 | 0 | 0 | 0 |
| 8/14/03 (6:07) | 265.5 | 255.7 | 20.3 | 120.0 | 65.7 | 99.758 | 0 | 0 | 0 | 0 |
| 8/14/03 (10:01) Start New Batch | 264.5 | 254.5 | 19.7 | 120.0 | 46.3 | 99.762 | 0.001 | 0.002 | 0.001 | 0 |
| 8/17/03 (3:22) | 246.8 | 160.1 | 20.0 | 119.5 | 1.5 | 77.868 | 2.026 | 2.644 | 3.775 | 3.085 |
| 8/17/03 (7:02) | 256.8 | 243.9 | 16.9 | 120.0 | 14.2 | 90.733 | 0.713 | 1.09 | 1.491 | 1.315 |
| 8/17/03 (12:05) | 256.2 | 243.5 | 16.6 | 120.0 | 13.5 | 94.476 | 0.362 | 0.633 | 0.844 | 0.79 |
| 8/17/03 (22:11) | 259.7 | 249.9 | 18.1 | 105.5 | 6.7 | 96.502 | 0.002 | 0.389 | 0.503 | 0.561 |
| 8/18/03 (7:03) | 259.7 | 250.1 | 18.1 | 115.1 | 9.8 | 97.547 | 0.119 | 0.266 | 0.335 | 0.416 |

| Date (Time) | 3-Ethyl Pentane | trans-1,2-Dimethyl-cyclopentane | Isooctane | C7 | Cis-1,2-Dimethyl-cyclopentane | Methyl-cyclo-hexane | Toluene | cis,cis-1,2,3-Trimethyl-cyclopentane |
|---|---|---|---|---|---|---|---|---|
| 7/25/03 (8:41) | 0 | 0.098 | 0.021 | 0 | 0.212 | 0 | 0 | 0 |
| 7/25/03 (10:10) | 0 | 0.102 | 0.024 | 0 | 0.215 | 0 | 0.002 | 0.001 |
| 7/25/03 (14:03) | 0 | 0.118 | 0.023 | 0 | 0.21 | 0 | 0 | 0 |
| 7/25/03 (18:13) | 0.087 | 0.315 | 0.035 | 0 | 0.021 | 0.088 | 0 | 0 |
| 7/26/03 (0:10) | 0.084 | 0.299 | 0.035 | 0 | 0.022 | 0.095 | 0.001 | 0 |
| 7/26/03 (8:39) | 0.11 | 0.402 | 0.028 | 0 | 0.019 | 0.063 | 0 | 0.001 |
| 7/26/03 (13:57) | 0.117 | 0.426 | 0.023 | 0 | 0.017 | 0.037 | 0 | 0 |
| 7/26/03 (18:02) | 0.116 | 0.423 | 0.023 | 0 | 0.017 | 0.037 | 0 | 0 |
| 7/26/03 (23:52) | 0.115 | 0.417 | 0.026 | 0 | 0.017 | 0.031 | 0.001 | 0 |
| 7/27/03 (7:53) | 0.113 | 0.399 | 0.021 | 0 | 0.016 | 0.029 | 0 | 0 |
| 7/27/03 (11:16) | 0.111 | 0.392 | 0.025 | 0 | 0.016 | 0.025 | 0.001 | 0 |
| 7/27/03 (18:07) | 0.1 | 0.345 | 0.021 | 0 | 0.017 | 0.027 | 0 | 0 |
| 7/27/03 (23:45) | 0.097 | 0.334 | 0.022 | 0 | 0.016 | 0.029 | 0 | 0 |
| 7/28/03 (6:30) | 0.319 | 0 | 0.022 | 0 | 0.016 | 0.028 | 0.001 | 0 |
| 7/28/03 (12:47) | 0.089 | 0.295 | 0.023 | 0 | 0.016 | 0.024 | 0 | 0 |
| 7/28/03 (18:09) | 0.266 | 0 | 0.024 | 0 | 0.016 | 0.027 | 0.001 | 0.001 |
| 7/28/03 (23:54) | 0.248 | 0 | 0.025 | 0 | 0.016 | 0.027 | 0.001 | 0.001 |
| 7/29/03 (6:31) | 0.23 | 0 | 0.02 | 0 | 0.018 | 0.025 | 0 | 0.001 |
| 7/30/03 (18:31) | 0.217 | 0 | 0.025 | 0 | 0.017 | 0.023 | 0 | 0 |
| 7/31/03 (14:27) | 0.231 | 0 | 0.023 | 0 | 0.016 | 0.023 | 0 | 0.001 |
| 7/31/03 (19:04) | 0.318 | 0 | 0.024 | 0 | 0.038 | 0.03 | 0 | 0 |
| 8/1/03 (7:36) | 0 | 0.183 | 0.035 | 0 | 0.07 | 0.076 | 0.001 | 0.001 |
| 8/1/03 (13:04) | 0.256 | 0.033 | 0 | 0 | 0.065 | 0.063 | 0.001 | 0.002 |

TABLE XVIII-continued

Fractionation Settings and Fractionation Product Results in Weight Percent

| Date (Time) | | | | | | | | |
|---|---|---|---|---|---|---|---|---|
| 8/1/03 (18:20) | 0 | 0.115 | 0.034 | 0 | 0.062 | 0.086 | 0.001 | 0 |
| 8/2/03 (0:02) | 0.015 | 0.03 | 0.047 | 0 | 0.04 | 0.18 | 0 | 0.002 |
| 8/2/03 (6:37) | 0 | 0.036 | 0.043 | 0 | 0.033 | 0.124 | 0 | 0.001 |
| 8/2/03 (12:05) | 0.02 | 0.041 | 0.001 | 0 | 0.025 | 0.046 | 0 | 0 |
| 8/2/03 (18:07) | 0 | 0.14 | 0.033 | 0 | 0.063 | 0.074 | 0 | 0.001 |
| 8/2/03 (23:52) | 0 | 0.296 | 0.031 | 0 | 0.064 | 0.06 | 0.003 | 0 |
| Start Batch Operation | | | | | | | | |
| 8/3/03 (6:16) | 0 | 0.037 | 0 | 37.81 | 0.057 | 0.014 | 0.045 | 0 |
| 8/3/03 (9:01) | 0 | 0.597 | 0.02 | 0 | 0.05 | 0.031 | 0.005 | 0.002 |
| 8/3/03 (15:07) | 0.407 | 0 | 0.012 | 0 | 0.026 | 0.011 | 0.002 | 0.001 |
| 8/3/03 (18:23) | 0.227 | 0 | 0.017 | 0 | 0.029 | 0.012 | 0.001 | 0 |
| 8/4/03 (0:09) | 0 | 0.022 | 0.001 | 0 | 0.017 | 0 | 0.001 | 0 |
| 8/4/03 (18:03) | 0 | 0.177 | 0.04 | 0 | 0.083 | 0.084 | 0 | 0 |
| 8/5/03 (18:22) | 0 | 0.681 | 0.019 | 0 | 0.035 | 0 | 0.001 | 0 |
| 8/6/03 (0:04) | 0 | 0.774 | 0.015 | 0 | 0 | 0.035 | 0.002 | 0.001 |
| 8/6/03 (5:39) | 0 | 1.03 | 0.012 | 0 | 0 | 0.023 | 0.001 | 0.001 |
| 8/6/03 (13:13) | 0.683 | 0 | 0.013 | 0 | 0 | 0.028 | 0 | 0 |
| 8/6/03 (18:31) | 0 | 0.263 | 0.025 | 0 | 0.043 | 0.04 | 0 | 0.001 |
| 8/7/03 (5:51) | 0.414 | 0 | 0.018 | 0 | 0.028 | 0.002 | 0 | 0 |
| Start New Batch | | | | | | | | |
| 8/8/03 (9:31) | 0.694 | 2.224 | 0.002 | 0 | 0 | 0.021 | 0 | 0.001 |
| 8/8/03 (18:16) | 0.437 | 1.322 | 0.014 | 0 | 0.001 | 0.03 | 0.001 | 0 |
| 8/8/03 (23:08) | 0 | 0.488 | 0.001 | 0 | 0 | 0.01 | 0 | 0 |
| 8/9/03 (6:18) | 0 | 0.44 | 0.002 | 0 | 0 | 0.011 | 0.001 | 0.001 |
| 8/9/03 (17:36) | 0 | 0.323 | 0 | 0 | 0.009 | 0 | 0.001 | 0.001 |
| 8/9/03 (23:27) | 0 | 0.18 | 0 | 0 | 0.009 | 0.002 | 0.003 | 0.001 |
| 8/10/03 (6:23) | 0 | 0.179 | 0.004 | 0 | 0.011 | 0 | 0.001 | 0 |
| 8/10/03 (11:42) | 0 | 0.086 | 0.006 | 0 | 0.014 | 0 | 0 | 0.002 |
| 8/10/03 (17:53) | 0.193 | 0 | 0 | 0 | 0 | 0.009 | 0 | 0.001 |
| 8/10/03 (23:42) | 0 | 0.239 | 0.001 | 0 | 0.008 | 0.001 | 0 | 0 |
| 8/11/03 (8:15) | 0.076 | 0 | 0 | 0 | 0.011 | 0.001 | 0 | 0.002 |
| 8/11/03 (12:36) | 0 | 0.026 | 0.007 | 0 | 0.017 | 0 | 0.001 | 0.001 |
| 8/11/03 (18:37) | 0.008 | 0.013 | 0.013 | 0 | 0.024 | 0 | 0.002 | 0.001 |
| 8/11/03 (23:11) | 0 | 0 | 0 | 0 | 0 | 0 | 0.001 | 0 |
| 8/12/03 (6:17) | 0.007 | 0.019 | 0.003 | 0 | 0.048 | 0.001 | 0.001 | 0.001 |
| 8/12/03 (11:24) | 0.024 | 0 | 0 | 0 | 0.018 | 0.002 | 0.001 | 0.001 |
| 8/12/03 (18:06) | 0.002 | 0.003 | 0.024 | 0 | 0.055 | 0.016 | 0 | 0.003 |
| 8/13/03 (0:05) | 0 | 0.022 | 0.001 | 0 | 0.001 | 0.002 | 0.002 | 0 |

TABLE XVIII-continued

Fractionation Settings and Fractionation Product Results in Weight Percent

| | | | | | | | | |
|---|---|---|---|---|---|---|---|---|
| 8/13/03 (5:45) | 0 | 0.021 | 0 | 0 | 0.005 | 0 | 0 | 0 |
| 8/13/03 (12:24) | 0 | 0.001 | 0 | 0.001 | 0.017 | 0 | 0.001 | 0.003 |
| 8/13/03 (18:46) | 0 | 0 | 0.035 | 0 | 0.068 | 0.018 | 0 | 0 |
| 8/13/03 (23:52) | 0 | 0.04 | 0 | 0 | 0.082 | 0.026 | 0.001 | 0 |
| 8/14/03 (6:07) | 0 | 0.056 | 0.001 | 0 | 0.04 | 0 | 0.001 | 0.002 |
| 8/14/03 (10:01) Start New Batch | 0.001 | 0.052 | 0 | 0 | 0.108 | 0.026 | 0.002 | 0 |
| 8/17/03 (3:22) | 2.373 | 7.455 | 0 | 0 | 0 | 0.002 | 0.001 | 0.001 |
| 8/17/03 (7:02) | 1.189 | 3.272 | 0 | 0 | 0 | 0.004 | 0.003 | 0.003 |
| 8/17/03 (12:05) | 0.792 | 1.993 | 0.001 | 0 | 0 | 0.002 | 0.001 | 0.004 |
| 8/17/03 (22:11) | 0 | 1.293 | 0 | 0 | 0 | 0.005 | 0.001 | 0 |
| 8/18/03 (7:03) | 0 | 0.914 | 0.002 | 0 | 0 | 0.004 | 0.001 | 0.002 |

Bromine Index data was also collected on samples from the streams recorded in Tables XVII and XIX. The Bromine Index was 11.3 for the reactor feed, 5.3 for the reactor effluent, 1.6 for the fractionation product, thus showing olefin elimination from the heptane between the reactor feed and fractionator product in the range of about 86 weight percent by Bromine Index.

While the present invention has been illustrated and described in terms of particular apparatus and methods of use, it is apparent that equivalent techniques and ingredients may be substituted for those shown, and other changes can be made within the scope of the present invention as defined by the appended claims.

The particular embodiments disclosed herein are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What we claim as our invention is:

1. A method of removing impurities from a heptane stream comprising:
    contacting the heptane stream with an acidic catalyst, wherein said contacting reduces a concentration of one or more close boiling impurities and one or more olefins in the heptane stream, and wherein the catalyst reduces the concentration of both the one or more close boiling impurities and the one or more olefins in a single contacting step.

2. The method of claim 1 wherein the concentration of olefins is reduced by at least about 25 percent by weight.

3. The method of claim 1 wherein said close boiling impurities comprise boiling points at a standard pressure of 760 Torr that are in the range of about 96.5 degrees to about 100.5 degrees Celsius.

4. The method of claim 1 wherein said close boiling impurities comprise boiling points at a standard pressure of 760 Torr that are in the range of about 97.0 to about 100.3 degrees Celsius.

5. The method of claim 1 wherein said close boiling impurities comprise boiling points at a standard pressure of 760 Torr that are in the range of about 97.5 to about 100.0 degrees Celsius.

6. The method of claim 1 wherein said close boiling impurities comprise cis-1,2-dimethylcyclopentane.

7. The method of claim 6 wherein a concentration of cis-1,2-dimethylcyclopentane in the heptane stream is reduced by at least about 25 percent by weight.

8. The method of claim 6 wherein a concentration of cis-1,2-dimethylcyclopentane in the heptane stream is reduced by at least about 70 percent by weight.

9. The method of claim 6 wherein a concentration of cis-1,2-dimethylcyclopentane in the heptane stream is reduced by at least about 85 percent by weight.

10. The method of claim 1 wherein said close boiling impurities comprise methylcyclohexane.

11. The method of claim 10 wherein a concentration of methylcyclohexane in the heptane stream is reduced by at least about 10 percent by weight.

12. The method of claim 1 wherein said heptane stream comprises at least about 90 weight percent n-heptane.

13. The method of claim 1 wherein said heptane stream comprises at least about 94 weight percent n-heptane.

14. The method of claim 1 wherein said heptane stream comprises a pure grade heptane.

15. The method of claim 1 wherein said heptane stream comprises at least 90 weight percent heptane, less than 1 weight percent cis-1,2-dimethylcyclopentane, and less than 1 weight percent methylcyclohexane.

16. The method of claim 1 further comprising drying said heptane stream prior to said contacting.

17. The method of claim 16 wherein said drying results in a moisture level in the heptane stream of no more than about 10 parts per million by weight.

18. The method of claim 1 further comprising fractionating the heptane stream after said contacting.

19. The method of claim 18 wherein said fractionating occurs at atmospheric pressure.

20. The method of claim 18 wherein said fractionating occurs at sub-atmospheric pressure.

21. The method of claim 18 wherein said fractionating occurs at super-atmospheric pressure.

22. The method of claim 21 wherein said fractionating occurs between 5 and 100 psig.

23. The method of claim 18 wherein said fractionating yields a heptane stream comprising at least about 99.75 weight percent n-heptane.

24. The method of claim 1 wherein said acidic catalyst comprises a compound selected from a group consisting of aluminum chloride, sulfuric acid, chlorosulfonic acid, sulfonated styrene-divinylbenzene copolymers, copolymers of perfluoroethylene with perfluorovinyl ether having attached sulfonyl acid groups, acid washed clay, "X" zeolites, "Y" zeolites, acidic "X" zeolites, acidic "Y" zeolites, LZY-84 zeolite and combinations of two or more thereof.

25. The method of claim 1 wherein said acidic catalyst comprises an LZY-84 acidic zeolite catalyst.

26. The method of claim 1 wherein said acidic catalyst comprises a Filtrol-24 acidized clay catalyst.

27. The method of claim 1 wherein said acidic catalyst comprises a liquid chlorosulfonic acid.

28. The method of claim 1 wherein said contacting occurs within a reactor.

29. The method of claim 28 wherein said reactor has a weight hourly space velocity of from about 0.1 to about 10.

30. The method of claim 28 wherein said reactor has a weight hourly space velocity of from about 1 to about 4.

31. The method of claim 28 wherein said reactor has a pressure sufficient to keep said heptane stream in the liquid phase.

32. The method of claim 28 wherein said reactor has a length to diameter ratio of from about 10 to about 25.

33. The method of claim 1 wherein said contacting results in a catalyst deactivation temperature range of from about 1 degree Celsius to about 10 degrees Celsius for about 1 weight percent of coke deposition.

34. The method of claim 1 wherein the acidic catalyst is a solid acidic catalyst.

35. The method of claim 34 wherein activity of the catalyst is regenerated by drying the catalyst.

36. The method of claim 34 wherein activity of the catalyst is regenerated by burning off coke.

37. The method of claim 36 wherein conditions effective for regenerating catalyst activity comprise temperatures from about 350 to about 600 deg. Celsius; an oxygen containing gas comprising from about 0.25 to about 10 percent, by volume, oxygen; and a time from about 4 to about 10 hours.

38. The method of claim 1 wherein the contacting isomerizes the close boiling impurity.

39. The method of claim 1 wherein the contacting isomerizes cis-1,2-dimethylcyclopentane into methylcyclohexane, trans-1,2-dimethylcyclopentane, or both.

* * * * *